(12) United States Patent
Wong et al.

(10) Patent No.: US 9,522,925 B2
(45) Date of Patent: Dec. 20, 2016

(54) SELECTIVE CANCER TRACKING ERADICATOR AND THE USES THEREOF

(71) Applicant: Hong Kong Baptist University, Hong Kong (HK)

(72) Inventors: Ka-Leung Wong, Hong Kong (HK); Wai-Kwok Wong, Hong Kong (HK); Rongfeng Lan, Hong Kong (HK); Tao Zhang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 14/934,140

(22) Filed: Nov. 5, 2015

(65) Prior Publication Data

US 2016/0130284 A1  May 12, 2016

Related U.S. Application Data

(60) Provisional application No. 62/077,312, filed on Nov. 9, 2014.

(51) Int. Cl.
| | |
|---|---|
| *C07F 5/00* | (2006.01) |
| *C07F 15/06* | (2006.01) |
| *A61K 41/00* | (2006.01) |
| *A61K 49/00* | (2006.01) |

(52) U.S. Cl.
CPC ............. *C07F 5/00* (2013.01); *A61K 41/008* (2013.01); *A61K 41/0071* (2013.01); *A61K 49/0036* (2013.01); *C07F 15/06* (2013.01)

(58) Field of Classification Search
CPC ........ C07F 5/00; C07F 15/06; A61K 41/0071; A61K 41/08; A61K 49/0036
See application file for complete search history.

(56) References Cited

PUBLICATIONS

Zhang et al. "Water-Soluble Mitochondria-Specific Ytterbium Complex with Impressive NIR Emission" Journal of the American Chemical Society, 2011, vol. 133, pp. 20120-20122.*
Kamkaew A, Lim SH, Lee HB, Kiew LV, Chung LY, Burgess K (2013) BODIPY dyes in photodynamic therapy. Chem Soc Rev 42, 77-88.
Liang X, Li X, Jing L, Yue X, Dai Z (2014) Theranostic porphyrin dyad nanoparticles for magnetic resonance imaging guided photodynamic therapy. Biomaterials 35, 6379-6398.
Hemmer E, Venkatachalam N, Hyodo H, Hattori A, Ebina Y, Kishimoto H, Soga K (2013) Upconverting and NIR emitting rare earth based nanostructures for NIR-bioimaging. Nanoscale 5, 11339-11361.
Kachynski AV, Pliss A, Kuzmin AN, Ohulchanskyy TY, Baev A, Qu J, Prasad PN (2014) Photodynamic therapy by in situ nonlinear photon conversion. Nature Photon 8, 455-461.
Celli JP, Spring BQ, Rizvi I, Evans CL, Samkoe KS, Verma S, Pogue B W, Haasan T (2010) Imaging and photodynamic therapy: mechanisms, monitoring and optimization. Chem Rev 110, 2795-2838.
Zhang JX, Li H, Chan CF, Lan R, Chan WL, Law GL, Wong WK, Wong KL (2012) A potential water-soluble ytterbium-based porphyrin-cyclen dual bio-probe for Golgi apparatus imaging and photodynamic therapy. Chem Comm 48, 9646-9648.
Collins HA, Khurana M, Moriyama EH, Mariampillai A, Dahlstedt E, Balaz M, Kuimova MK, Drobizhev M, Yang VXD, Phillips D, Rebane A, Wilson BC, Anderson HL (2008) Blood-vessel closure using photosensitizers engineered for two-photon excitation. Nature Photon 2, 420-424.
Bonneaua S, Morlière P, Brault D (2004) Dynamics of interactions of photosensitizers with lipoproteins and membrane-models: correlation with cellular incorporation and subcellular distribution. Biochem Pharmaco. 68, 1443-1452.
Zhang JX, Chan CF, Zhou JW, Lau TCK, Kwong DWJ, Tam HL, Mak NK, Wong KL, Wong WK (2012) Comparative studies of the cellular uptake, subcellular localization, and cytotoxic and phototoxic antitumor properties of ruthenium (II)-porphyrin conjugates with different linkers. Bioconjug Chem 23, 1623-1638.
D'Souza GGM, Wagle MA, Saxena V, Shah A (2011) Approaches for targeting mitochondria in cancer therapy. BBA—Bioenergetics 1807, 689-696.

(Continued)

*Primary Examiner* — Joseph Kosack
(74) *Attorney, Agent, or Firm* — Ella Cheong Hong Kong; Sam T. Yip

(57) ABSTRACT

The present invention discloses a new modality of photodynamic therapy (PDT) through the design of the present invention's truly dual-functional—PDT and imaging—gadolinium complex (Gd—N) with a molecular formula of:

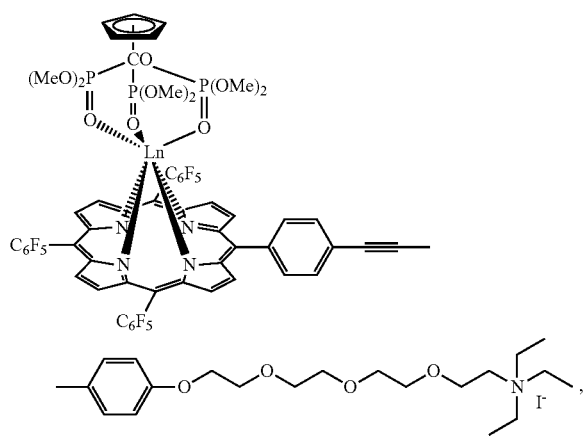

which can target cancer, cells specifically. The present invention provides a PDT drug that can specifically localize on the anionic cell membrane of cancer cells in which its laser-excited photoemission signal can be monitored without triggering the phototoxic generation of reactive oxygen species—singlet oxygen—prior to due excitation. The present invention also provides the use of Gd—N as a tumor selective PDT photosensitizer modality.

10 Claims, 15 Drawing Sheets

(56) References Cited

PUBLICATIONS

Zhang T, Chan CF, Hao JH, Law GL, Wong WK and Wong KL (2013). Fast Uptake, water-soluble, mitochondria-specific erbium complex for dual function molecular probe—imaging and photodynamic therapy. RSC Adv 3, 382-385. and supplementary information.

Schmidt R, Afshari E (1990) Comment on "Effect of solvent on the phosphorescence rate constant of singlet molecular oxygen (1.DELTA.g)". J Phys Chem 94, 4377-4378.

Khalil GE, Thompson EK, Gouterman M, Callis JB, Dalton LR, Turro NJ, Jockusch S (2007) NIR luminescence of gadolinium porphyrin complexes. Chem Phys Lett 435, 45-49.

Zhang T, Chan CF, Lan R, Li H, Mak NK, Wong WK, Wong KL (2013) Porphyrin-based ytterbium complexes targeting anionic phospholipid membranes as selective biomarkers for cancer cell imaging. Chem Comm 49, 7252-7254.

P Hinnen, FWW de Rooij, MLF van Velthuysen, A Edixhoven, R van Hillegersberg, HW Tilanus, JHP Wilson and PD Siersema (1998) Biochemical basis of 5-aminolaevulinic acid-induced protoporphyrin IX accumulation: a study in patients with (pre)malignant lesions of the oesophagus. Br J Cancer 78, 683-685.

Idris NM, Gnanasammandhan MK, Zhang J, Ho PC, Mahendran R, Zhang Y (2012) In vivo photodynamic therapy using upconversion nanoparticles as remote-controlled nanotransducers. Nature Med 18, 1580-1585.

Ferrario A, Rucker N, Wong S, Luna M, Gomer CJ (2007) Survivin, a member of the inhibitor of apoptosis family, is induced by photodynamic therapy and is a target for improving treatment response. Cancer Res 67, 4989-4995.

Wong WK, Zhang LL, Wong WT, Xue F, Mak TCW (1999) Synthesis and crystal structures of cationic lanthanide(III) monoporphyrinate complexes. J Chem Soc Dalton Trans 615-622.

Strachan JP, Gentemann S, Seth J, Kalsbeck WA, Lindsey JS, Holten D, Bocian DF (1997) Effects of orbital ordering on electronic communication in multiporphyrin arrays. J Am Chem Soc 119, 11191-11201.

Jiang FL, Wong WK, Zhu XJ, Zhou GJ, Wong WY, Wu PL, Tam HL, Cheah KW, Ye C, Liu Y (2007) Synthesis, characterization, and photophysical properties of some heterodimetallic bisporphyrins of ytterbium and transition metals—enhancement and lifetime extension of Yb3+ emission by transition-metal porphyrin sensitization. Eur J Inorg Chem 3365-3374.

Zhang T, Zhu X, Cheng CCCW, Kwok WM, Tam HL, Hao J, Kwong DWJ, Wong WK, Wong KL (2011) Water-soluble mitochondria-specific ytterbium complex with impressive NIR emission. J Am Chem Soc 133, 20120-20122.

Zhang T, Chan CF, Lan R, Li H, Mak NK, Wong WK, Wong KL (2013) Porphyrin-based ytterbium complexes targeting anionic phospholipid membrane as selective biomarkers for cancer cell imaging. Chem Commun 49, 7252-7254.

Kim KS, Lim JM, Osuka A, Kim D (2008) Various strategies for highly-efficient two-photon absorption in porphyrin arrays. J Photochem Photobio. C Photochem Rev 9, 13-28.

* cited by examiner

SELECTIVE CANCER TRACKING ERADICATOR AND THE USES THEREOF

CROSS-REFERENCE TO RELATED APPLICATIONS

The present application claims priority of U.S. provisional application No. 62/077,312 filed on Nov. 9, 2014 and which the disclosure is hereby incorporated by reference.

TECHNICAL FIELD

The present invention relates to a new modality of photodynamic therapy (PDT) through the design of the present invention's truly dual-functional—PDT and imaging—gadolinium complex (Gd—N) which can target cancer cells specifically. The present invention provides a PDT drug that can specifically localize on the anionic cell membrane of cancer cells in which its laser-excited photoemission signal can be monitored without triggering the phototoxic generation of reactive oxygen species—singlet oxygen—prior to due excitation. The present invention also provides the use of Gd—N as a tumor selective PDT photosensitizer modality.

BACKGROUND

Significant challenges of tumor cells recognition, in-depth light penetration and in situ monitoring are confronted by scientists to develop photodynamic therapy (PDT) as reliable clinical treatment for cancers. To address the penetration depth and molecular imaging issues, the utilization of near-infrared (NIR) excitation (via multi-photon/up-conversion processes) and emission within the "biological windows" (such as $1^{st}$ window: 600-950 nm, $2^{nd}$ window: 1-1.35 μm and $3^{rd}$ window: 1.5-1.8 μm) has provided a satisfying resolution since NIR photons can penetrate deep into the tissue and re-emit sharply without being absorbed by the cell even in the blood media and causing damage. Clear images can be obtained and differentiated then from the usual biological auto-fluorescence background. Recently, two-photon absorption photodynamic therapy (TPA-PDT) has received increasing attention. Porphyrin-based photosensitizers are considered as the prime candidates as their two-photon (TP) induced singlet oxygen ($^1O_2$) generation and red/near-infrared emission (~650 nm & ~750 nm) are very efficient and intense. Several design strategies for TPA-PDT photosensitizers have been reported in the literature, but only very few of those compounds are tumor cell-specific or have been investigated in vitro and in vivo, concerning especially porphyrins and lanthanides. For instance, selective closure of blood vessels through two-photon excitation PDT in vivo using porphyrin dimers of large TP absorption cross section has been demonstrated currently; tumor selectivity of amphiphilic photosensitizers has also been found related to their efficient binding to low-density lipoproteins which are responsible for the transport of porphyrins to tumor tissues. High molecular-weight porphyrins, in essence, preferentially accumulate on solid tumors and are expected to be internalized into membrane-limited organelles, thereby achieving controlled localization in the intercellular compartment. However, it has still been arduous for PDT probes to come into contact with cancer cells in particular, with two major problems being associated with commercially available or literature-reporting photosensitizers for photodynamic treatment: (i) the recognition of cancer cells and (ii) the monitoring of their effectiveness. In this regard, the Applicants of the present invention had reported previously in Zhang T, Chan C F, Hao J H, Law G L, Wong W K and Wong K L (2013). *Fast Uptake, water-soluble, mitochondria-specific erbium complex for dual function molecular probe—imaging and photodynamic therapy. RSC Adv* 3, 382-385, a specific phospholipid marker—an ytterbium-porphyrin complex (Yb—N) which has a strong binding with anionic phospholipid species in solution and can identify several of them in a number of cancer cells via long-lived visible-to-NIR lanthanide luminescence. A limitation of this complex is that it does not photo-generate $^1O_2$. Without the advances in stem cell and gene therapy against cancers for 100% efficiency, it is always essential to explore any potential alternative methodology for the sake of human well-being.

It is an objective of the present invention to provide for PDT probes that solve the following three problems, namely (i) the recognition of cancer cells; (ii) the monitoring of their effectiveness and (iii) photo-generating $^1O_2$—singlet oxygen.

SUMMARY OF THE INVENTION

In a first aspect of the present invention there is provided a composition for photodynamic therapy and imaging of cancer cells comprising gadolinium complex with a molecular formula of:

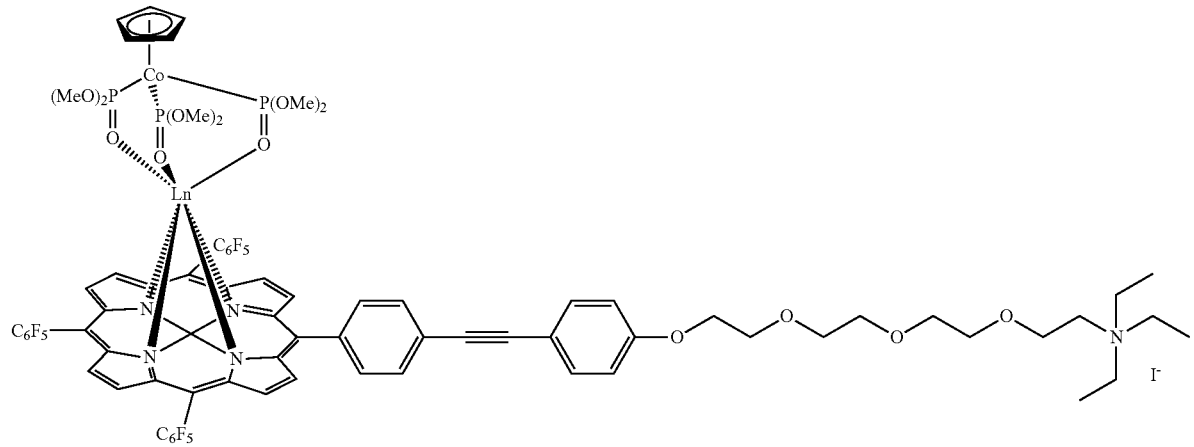

wherein Ln=Gd, such as gadolinium porphyrinate (Gd—N) or a pharmaceutically acceptable salt thereof.

In a first embodiment of the first aspect of the present invention there is provided a composition for photodynamic therapy and imaging of cancer cells wherein the cancer cells have anionic cell membranes.

In a second aspect of the present invention there is provided a method of photodynamic therapy and imaging of cancer cells using the composition according to the first aspect of the present invention wherein said composition is administered to a subject in need thereof and a radiation source is used to irradiate the cancer cells in the subject in need thereof.

In a first embodiment of the second aspect of the present invention there is provided a method of photodynamic therapy and imaging of cancer cells comprising administering to a subject in need thereof a composition according to the first aspect of the present invention and irradiating the cancer cells in the subject in need thereof with a radiation source, wherein the administration of said composition is performed intravenously or by injection to site of said cancer cells.

In a second embodiment of the second aspect of the present invention there is provided a method of photodynamic therapy and imaging of cancer cells comprising administering to a subject in need thereof a composition according to the first aspect of the present invention and irradiating the cancer cells in the subject in need thereof with a radiation source, wherein said radiation source is a light source of about 860 nm in wavelength.

In a third aspect of the present invention there is provided a method of synthesizing the composition according to the first aspect of the present invention comprising steps according to the scheme 1:

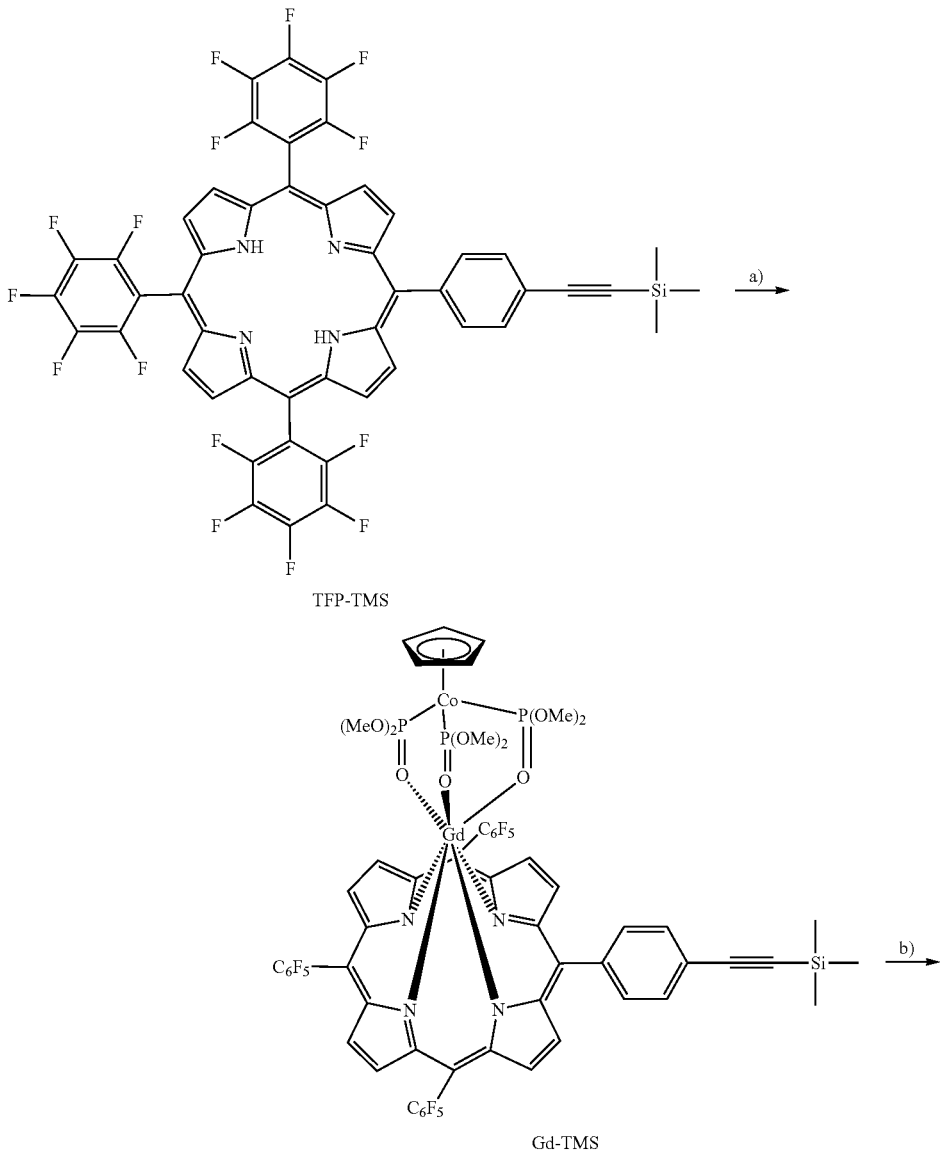

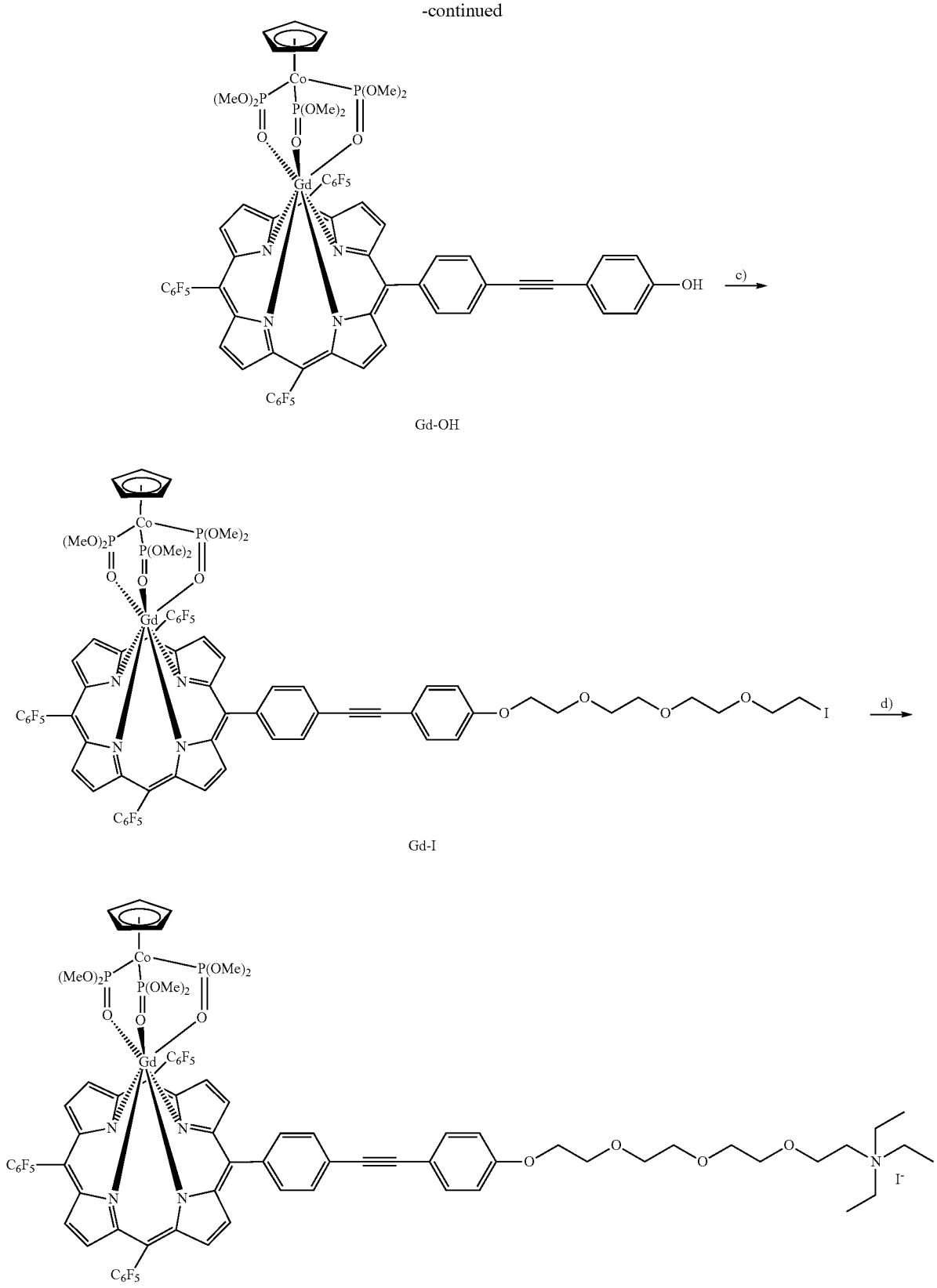
a) (i) Gd[N(SiMe$_3$)$_2$]$_3$·[LiCl(THF)$_3$]$_x$, toluene, reflux, 12 h; (ii) Na{($\eta^5$-C$_5$H$_5$)Co[P(=O)(OMe)$_2$]$_3$}, toluene, rt, 1 h; b) (i) TBAF (THF, 1M), CH$_2$Cl$_2$, rt, 30 min; (ii) a) 4-iodophenol, Pd(PPh$_3$)$_4$, CuI, THF, NEt$_3$, 40° C., 12 h; c) Tetraethyleneglycol diiodide, DMF, K$_2$CO$_3$, 80° C., 8 h; d) Triethylamine, DMF, 85° C., 24 h.

wherein

Step a): Removing the solvent from a solution of Gd[N(SiMe$_3$)$_2$]$_3$·[Li(THF)$_3$Cl]$_x$ to form a precipitation of LiCl; adding dichloromethane (CH$_2$Cl$_2$) to the precipitation of LiCl to form a first mixture wherein the first mixture is centrifuged to separate a clear layer from said first mixture; transferring the clear layer to a porphyrin free base TFP-TMS dissolved in toluene solution to form a second mixture; refluxing the second mixture until most of the free base is coordinated with the metal ion to form a refluxed second mixture; cooling the refluxed second mixture to room temperature to form a cooled refluxed second mixture; adding dry Na{($\eta^5$-C$_5$H$_5$)Co[P(=O)(OMe)$_2$]$_3$} to the cooled refluxed second mixture to form a third mixture; stirring the third mixture; removing the solvent from the third mixture to form a first residue; dissolving the first residue in CH$_2$Cl$_2$ to form a fourth mixture; filtering and column chromatographing the fourth mixture using CH$_2$Cl$_2$/Hexane as eluent to produce Gd-TMS;

Step b): Adding Tetrabutylammonium fluoride to a solution of the Gd-TMS in CH$_2$Cl$_2$, and stirring the solution to create a chemical reaction; after completion of the chemical reaction, the solution is passed through column chromatography to form a fifth mixture; removing solvent from the fifth mixture to obtain an intermediate; dissolving the intermediate and 4-iodophenol in dry tetrahydrofuran and triethylamine to form a sixth mixture; mixing the sixth mixture with nitrogen to form a nitrogenized sixth mixture; adding Pd(PPh$_3$)$_4$ and CuI to said nitrogenized sixth mixture to form a seventh mixture; stirring the seventh mixture at least 35° C. for at least 10 hours under a nitrogen atmosphere to produce a stirred seventh mixture; removing the solvent from the stirred seventh mixture to produce a second residue; purifying the second residue using column chromatography with CH$_2$Cl$_2$/Methanol as eluent to produce Gd—OH;

Step c): Adding anhydrous K$_2$CO$_3$ to a solution of Gd—OH and tetraethyleneglycol diiodide in dry N,N-Dimethylmethanamide to form an eighth mixture; heating said eighth mixture to at least 80° C. for at least 8 hours under a nitrogen atmosphere to form a heated eighth mixture; removing the solvent from the heated eighth mixture to form a first crude product; purifying the first crude product using column chromatography eluented by CH$_2$Cl$_2$/CH$_3$OH to produce Gd—I, and Step d): Adding anhydrous NEt$_3$ to a solution of Gd—I in dry DMF to form a ninth mixture; heating the ninth mixture to at least 85° C. for at least 24 hours under nitrogen atmosphere to form a heated ninth mixture; removing the solvent from the heated ninth mixture to obtain a second crude product; purifying the second crude product using column chromatography with CH$_2$Cl$_2$/CH$_3$OH as the eluent to remove unreacted Gd—I and other impurities, then further purifying with CH$_2$Cl$_2$/CH$_3$OH as the eluent to obtain Gd—N.

In a first embodiment of the third aspect of the present invention there is provided a method of synthesizing the composition according to the first aspect of the present invention wherein the steps of removing the solvent from a given mixture or solution is done in a vacuum.

In a second embodiment of the third aspect of the present invention there is provided a method of synthesizing the composition according to the first aspect of the present invention wherein the process of mixing the sixth mixture with nitrogen to form a nitrogenized sixth mixture in step b) is by bubbling nitrogen gas in said sixth mixture for at least 30 minutes.

In a third embodiment of the third aspect of the present invention there is provided a method of synthesizing the composition according to the first aspect of the present invention wherein the process of using column chromatography in steps a) to d) are column chromatography on silica gel.

In a fourth embodiment of the third aspect of the present invention there is provided a method of synthesizing the composition according to the first aspect of the present invention wherein the volume/volume of the column chromatography with CH$_2$Cl$_2$/CH$_3$OH of step d) is first 80:1 and followed by 10:1.

Features, integers, characteristics, compounds, chemical moieties or groups described in conjunction with a particular aspect, embodiment or example of the present invention are to be understood to be applicable to any other aspect, embodiment or example described herein unless incompatible therewith.

Those skilled in the art will appreciate that the present invention described herein is susceptible to variations and modifications other than those specifically described.

The present invention includes all such variation and modifications. The present invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

The present invention is not to be limited in scope by any of the specific embodiments described herein. The following embodiments are presented for exemplification only.

Without wishing to be bound by theory, the Applicants of the present invention have developed gadolinium porphyrinate (Gd—N), a PDT agent which had been synthesized on the basis of Yb—N and shown 51% singlet oxygen quantum yield with characteristic NIR emission of the porphyrin upon photoexcitation. (FIG. 1a) Comprehensive studies of it have revealed that Gd—N can recognize tumor cells by their anionic phosphotidylserine membrane in the first six dosed hours, and that upon administration laser-irradiation at certain wavelengths, it can enter the tumor cells and produce $^1O_2$ in addition to exhibiting TP-induced NIR emission. Results of the in vivo mouse models and biodistribution assays have further illustrated that Gd—N was found to be located in the tumor after simple injection of Gd—N into the blood vessel. Upon $^1O_2$ releasing from the porphyrin, the solid tumor was found to be reduced after 24-hour treatment. To the best of current knowledge in the art, there is a dearth of examples of in vivo lanthanide-based PDT agents in the literature. The Gd—N of the present invention can, therefore, serve as the very blueprint for the development of next-generation smart PDT agents with the use of lanthanide porphyrinates for practical cancer tracking, imaging and killing.

Results and Discussion

Figure 2:
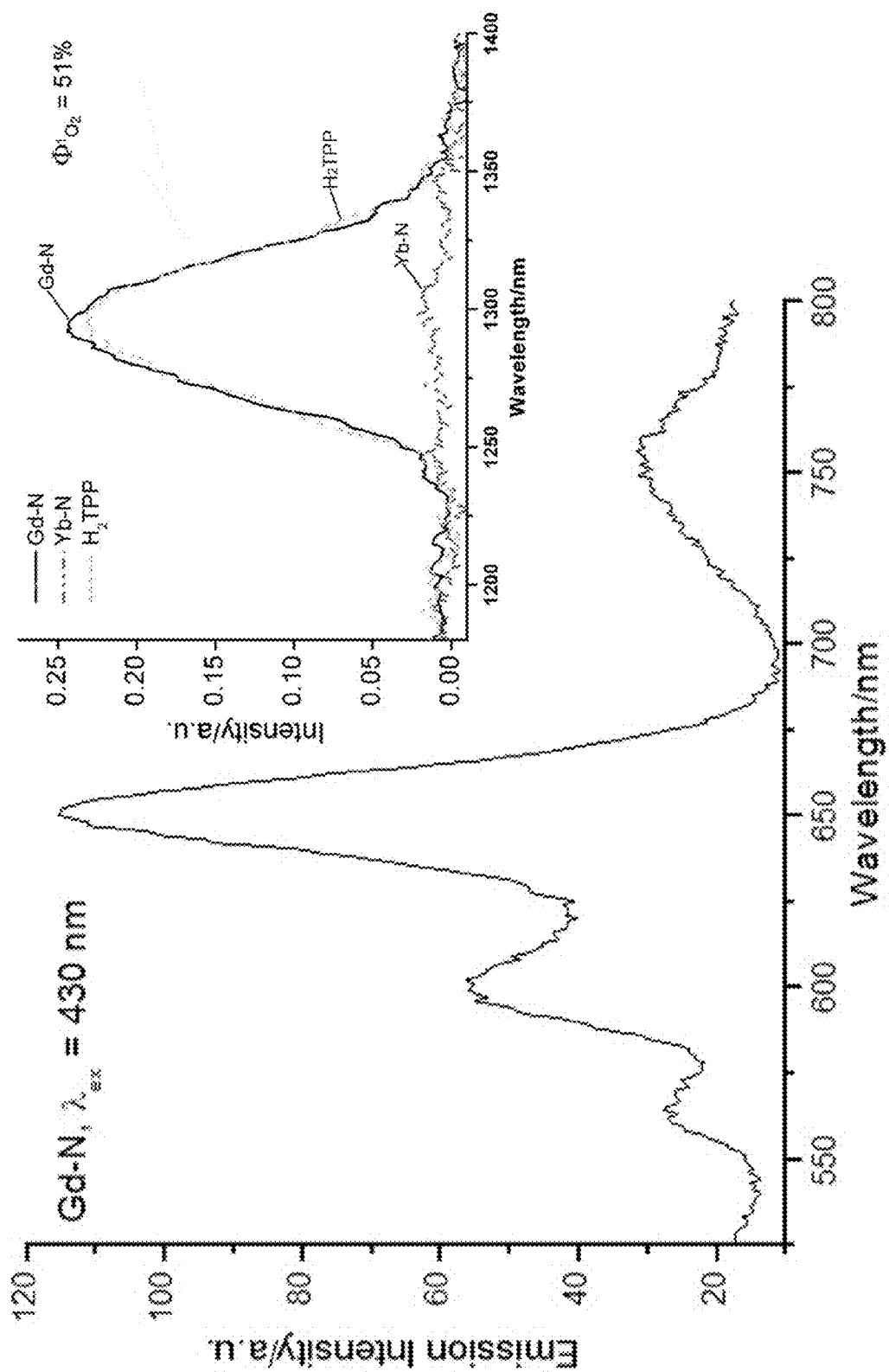
FIG. 2 shows the emission spectra of Gd—N (HEPES buffer solution, 10 μM, $\lambda_{ex}$=430 nm, pH=7.4) and $^1O_2$ quantum yield measurement (Near-IR phosphorescence spectra of $^1O_2$ CHCl$_3$, 10 μM, $\lambda_{ex}$=430 nm, abs($\lambda_{ex}$)=0.03). Yb—N and H$_2$TPP were measured similarly as control.
Figure 8:
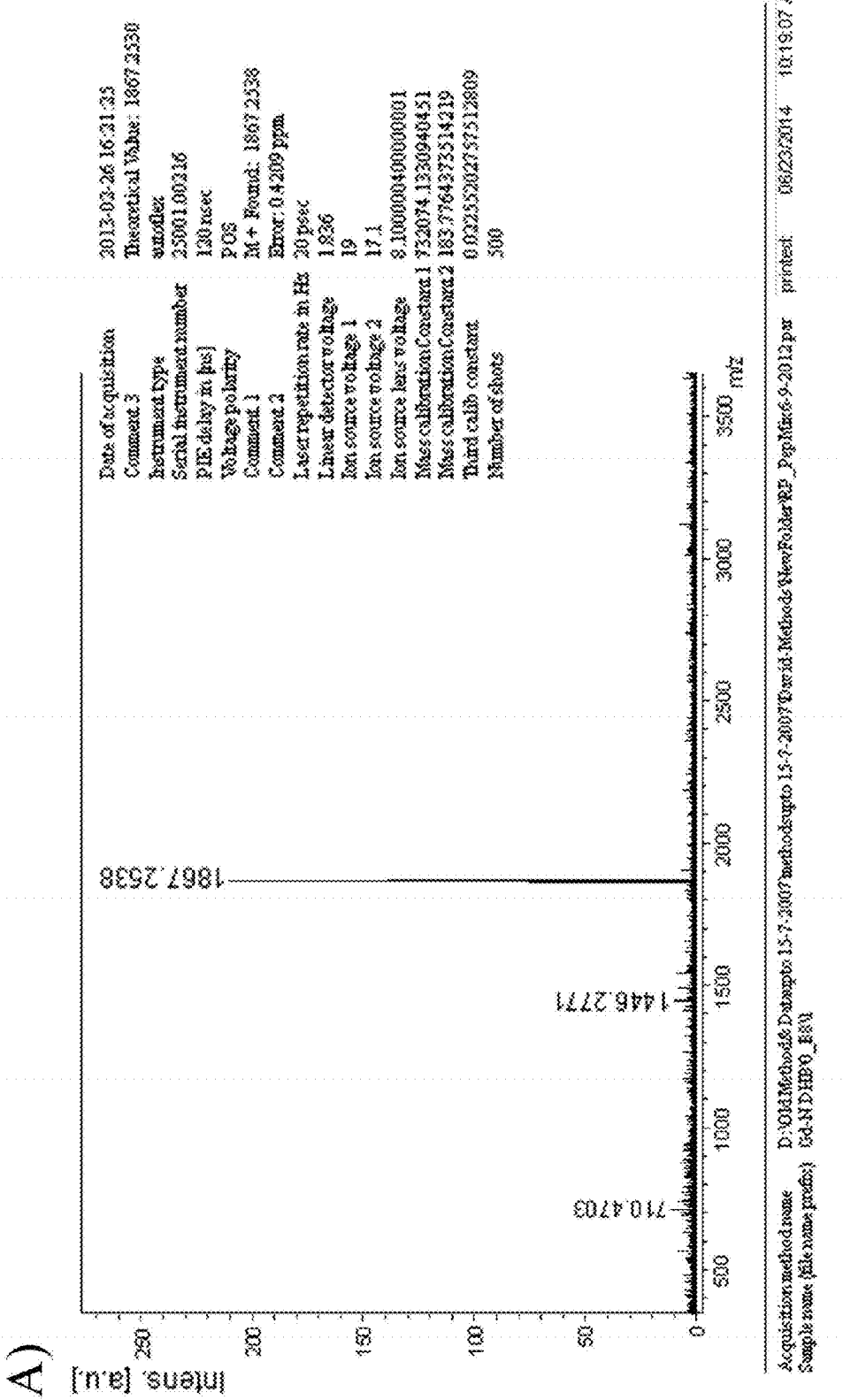
FIG. 8 shows A) High-resolution MALDI-TOF mass spectrum of Gd—N; B) Isotopic patterns for the molecular ion; C) Calculated MS patterns of the molecular ion Gd—N (using the software: IsoPro 3.0).
Figure 8:
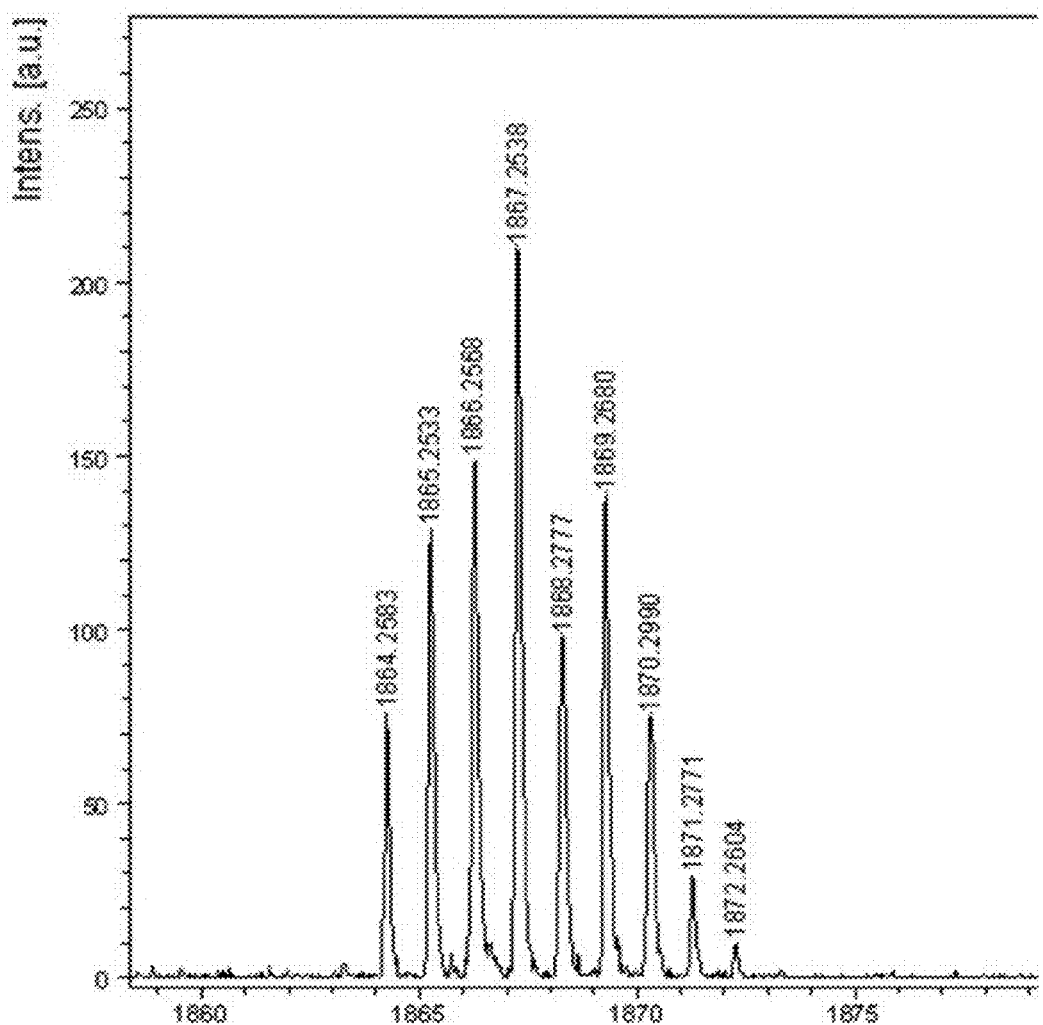
Figure 8:
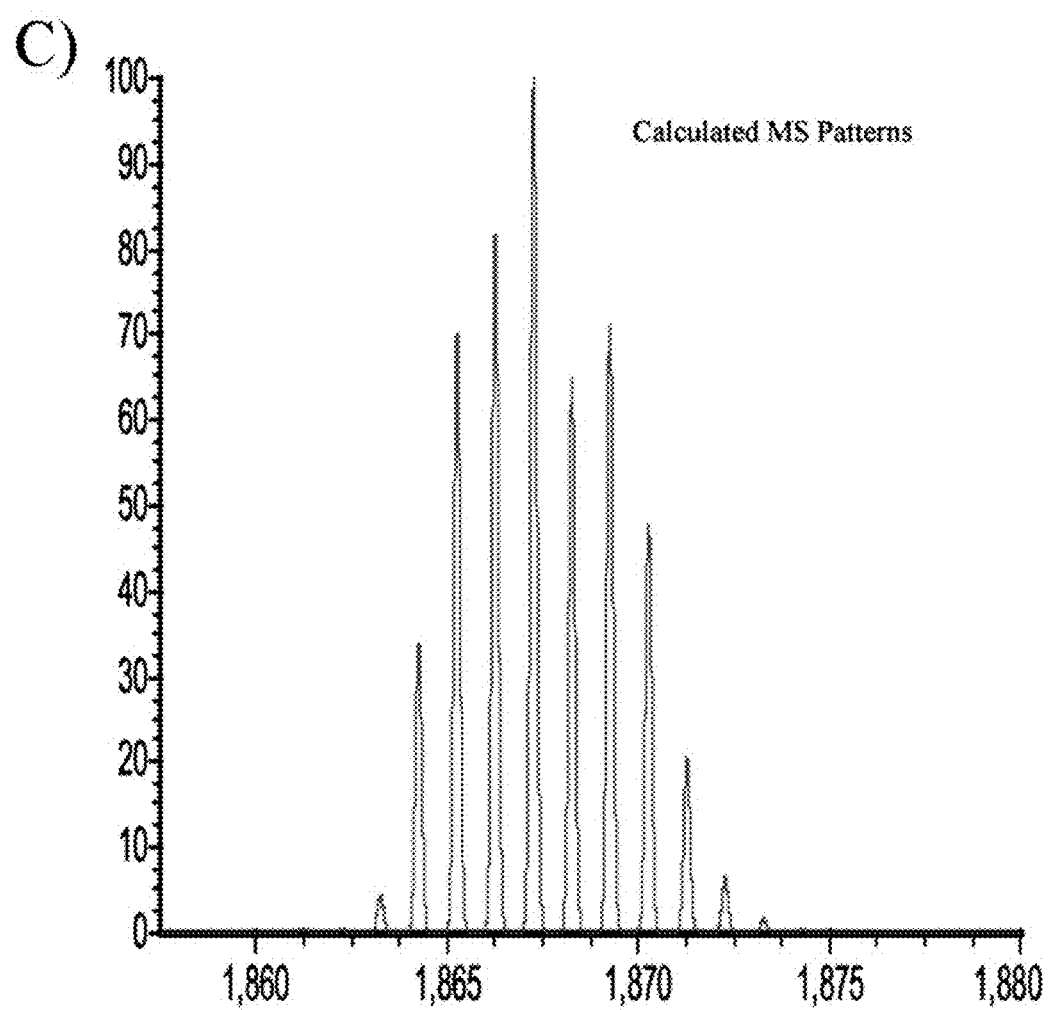
Figure 9:
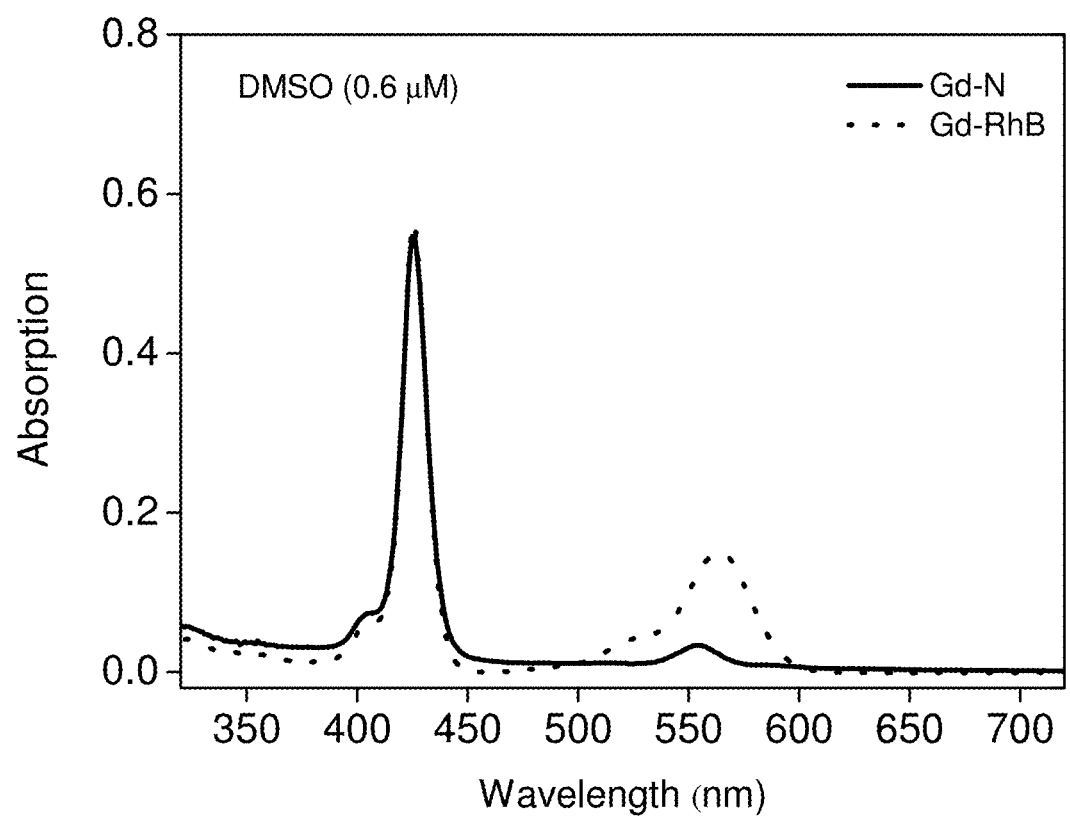
FIG. 9 shows the absorption spectra of Gd—N and Gd—RhB.
Figure 10:
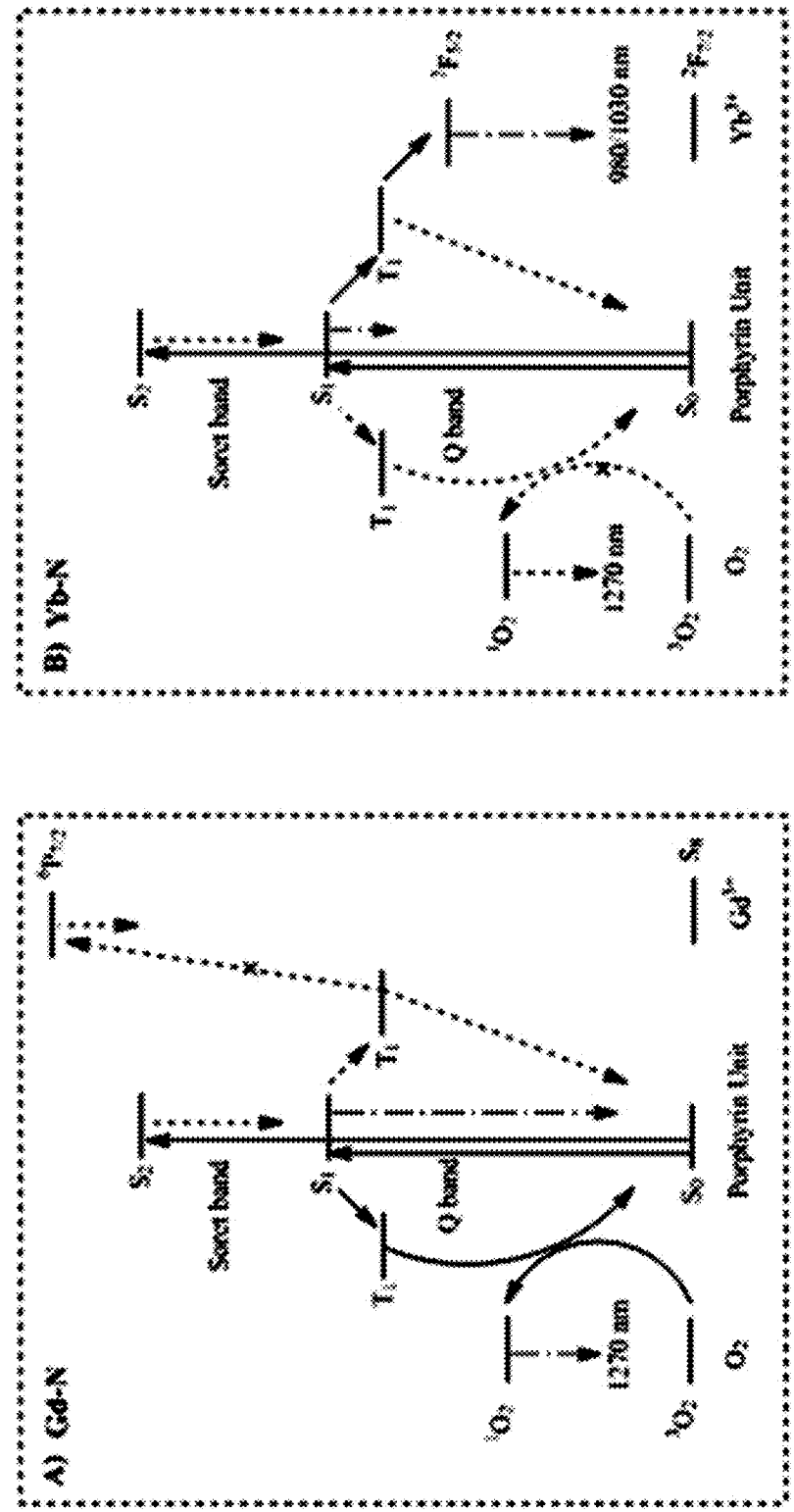
FIG. 10 shows the schematic representation of energy absorption, migration and emission (indicated by -•-•- ▶) processes in the (A) gadolinium porphyrinate complex (Gd—N) and (B) ytterbium porphyrinate complex (Yb—N).
Figure 11:
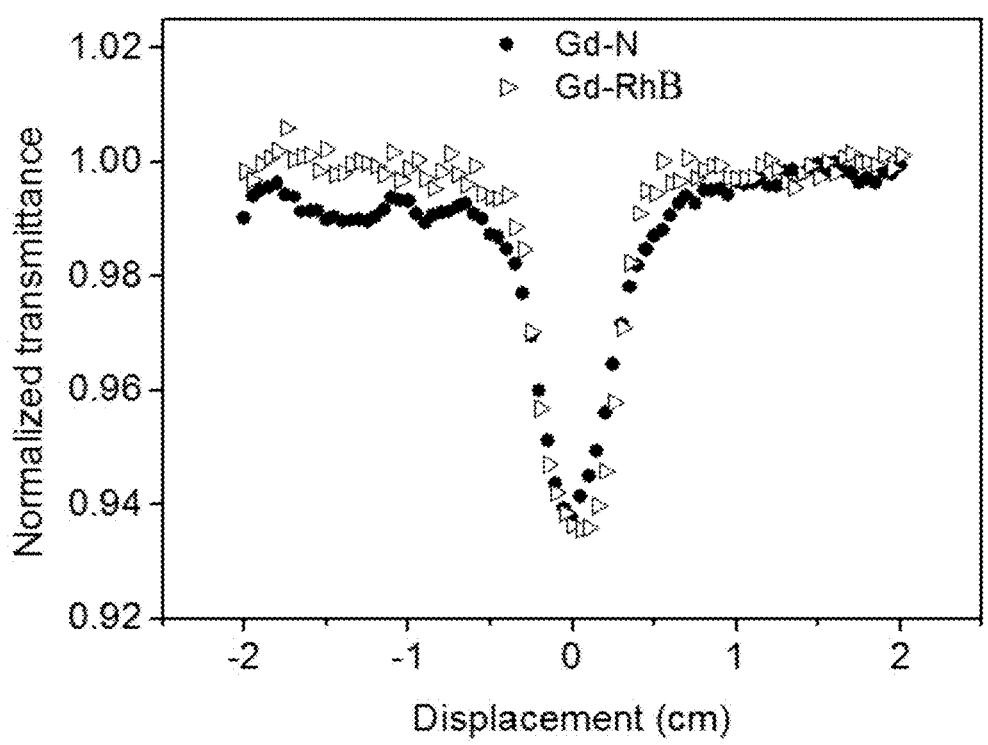
FIG. 11 shows the open-aperture Z-scan trace of Gd—N (351 GM) and Gd—RhB (418 GM) excited at 800 nm in DMSO (5 μM). The average power of the laser beam was 0.271 mW.

The detailed synthesis and characterization of Gd—N, which is the motif structure of the ytterbium complex (Yb—N) reported in the inventors' previous work, can be referred to the information provided in Scheme 1 and FIG. 8. Gd—N and Yb—N are structurally more or less identical (the vector ligated to Gd—N is also the same as Yb—N), except for the lanthanide ion present in the complex. It is self-evident that porphyrin's coordination with different lanthanides can cause changes in not merely the NIR emission from itself, yet also the $^1O_2$ generation simultaneously. (FIG. 2 and FIG. 9) Such phenomena, in principle, arise from the fact that better orbital overlapping between the metal center and the ligand results in better energy transfer (i.e. the bonding orbitals of Yb which consists of a smaller atomic radius than Gd is thus overlap more preferably and compatibly with the porphyrin's orbitals). The heavy atom effect exerted by the lanthanide can also augment the triplet-state decay rate and lead to higher triplet-state quantum yields of the porphyrin system. According to the spectroscopic studies, the singlet oxygen quantum yield of Yb—N was measured to be 0% and Gd—N was determined to be 51%. The calculations were based on (i) the NIR phosphorescence intensity of the $^1O_2$ (at 1270 nm) produced from the two complexes and (ii) the lowest excited states of ytterbium $^2F_{5/2}$ (~10200 cm$^{-1}$) and gadolinium $^6P_{7/2}$ (~32000 cm$^{-1}$) respectively. It should be noted that the latter energy level of $^6P_{7/2}$ is much higher than the singlet/triplet levels of the porphyrin unit (singlet states=~23200 and 15300 cm$^{-1}$; triplet state=12500 cm$^{-1}$). An assumption does has it that for such a large energy gap between porphyrin and Gd, there is no energy transfer from porphyrin to Gd; the energy gained can therefore purely be either dissipated in the form of light or employed to form singlet oxygen, making direct determination of $^1O_2$ quantum yield feasible. (FIG. 10A) This is entirely not the same case for Yb. As the energy gap between porphyrin and Yb is small, most of the energy absorbed by the porphyrin unit would just be simply transferred to the ytterbium efficiently (via heavy atom effect) and afford the characteristic f-f emission exclusively. (FIG. 10B) The two percentages have clearly showcased that nearly half part of the energy absorbed by the porphyrin of Gd—N would be involved in the $^1O_2$ generation, while the rest will be normally used for the porphyrin's NIR emissions; in contrast, for Yb—N, ytterbium's f-f luminescence at 1.08 μm is the dominant process of energy consumption under the same photoexcitation. (Linear and two-photon excitation at 430 nm and 860 nm respectively; the two-photon absorption cross section of Gd—N and Yb—N are similar to be ~351 GM (FIG. 11). With respect to the measurements in FIG. 10 the following approach was taken: "According to the spectroscopic studies, the singlet oxygen quantum yield of Yb—N was measured to be 0% and Gd—N was determined to be 51%. The calculations were based on (i) the NIR phosphorescence intensity of the $^1O_2$ (at 1270 nm) produced from the two complexes and (ii) the lowest excited states of ytterbium $^2F_{5/2}$ (~10200 cm$^{-1}$) and gadolinium $^6P_{7/2}$ (~32000 cm$^{-1}$) respectively. It should be noted that the latter energy level of $^6P_{7/2}$ is much higher than the singlet/triplet levels of the porphyrin unit (singlet states=~23200 and 15300 cm$^{-1}$; triplet state=12500 cm$^{-1}$). An assumption does has it that for such a large energy gap between porphyrin and Gd, there are no energy transitions available; the energy gained can therefore purely be either dissipated in the form of light or employed to form singlet oxygen, making direct determination of singlet oxygen quantum yield feasible. (FIG. 10 A). This is entirely not the same case as Yb that most of the energy absorbed by the porphyrin unit would just be simply transferred to the ytterbium efficiently (via heavy metal effect) and afford the characteristic f-f emission exclusively. (FIG. 10 B) The two percentages have clearly showcased that nearly half part of the energy absorbed by the porphyrin of Gd—N would be involved in the $^1O_2$ generation, while the rest will be normally used for the porphyrin's NIR emissions; in contrast, for Yb—N, ytterbium's f-f luminescence at 1.08 μm is the dominant process of energy consumption under the same photoexcitation."

Figure 1:
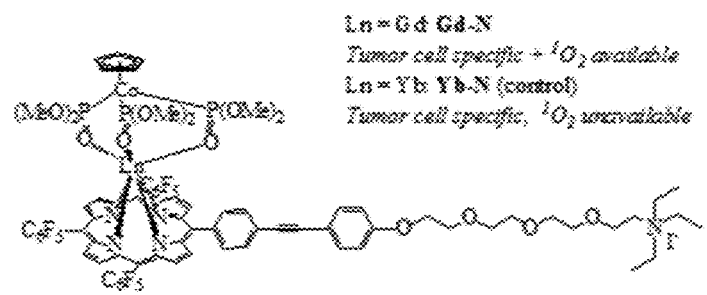
FIG. 1 shows a) The molecular structure of the smart cancer cells specific photodynamic therapy agent (Gd—N) and their control analogues Yb—N and Gd—RhB; b) the 3D in vitro imaging of Gd—N after 15-hour incubation in HeLa cells; c) and d) the difference in subcellular localization of Gd—N in cancer cells (HeLa) and normal cells. (WPMY-1).
Figure 1:
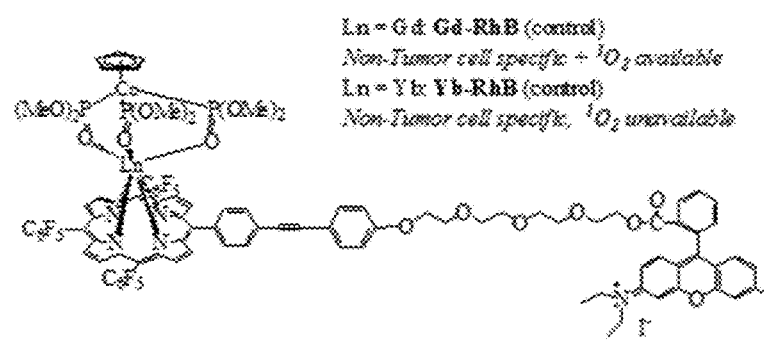
Figure 1:
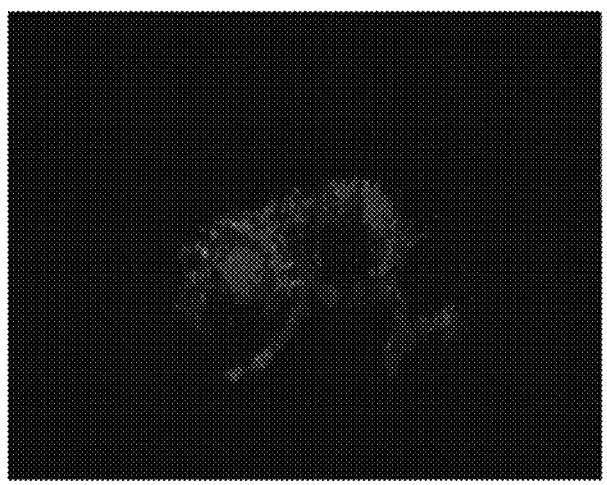
Figure 1:
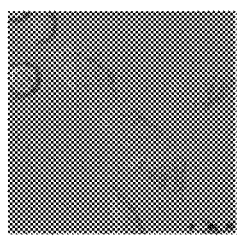
Figure 1:
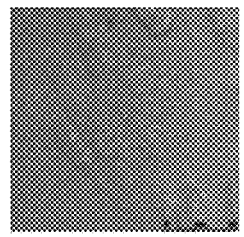
Figure 3:
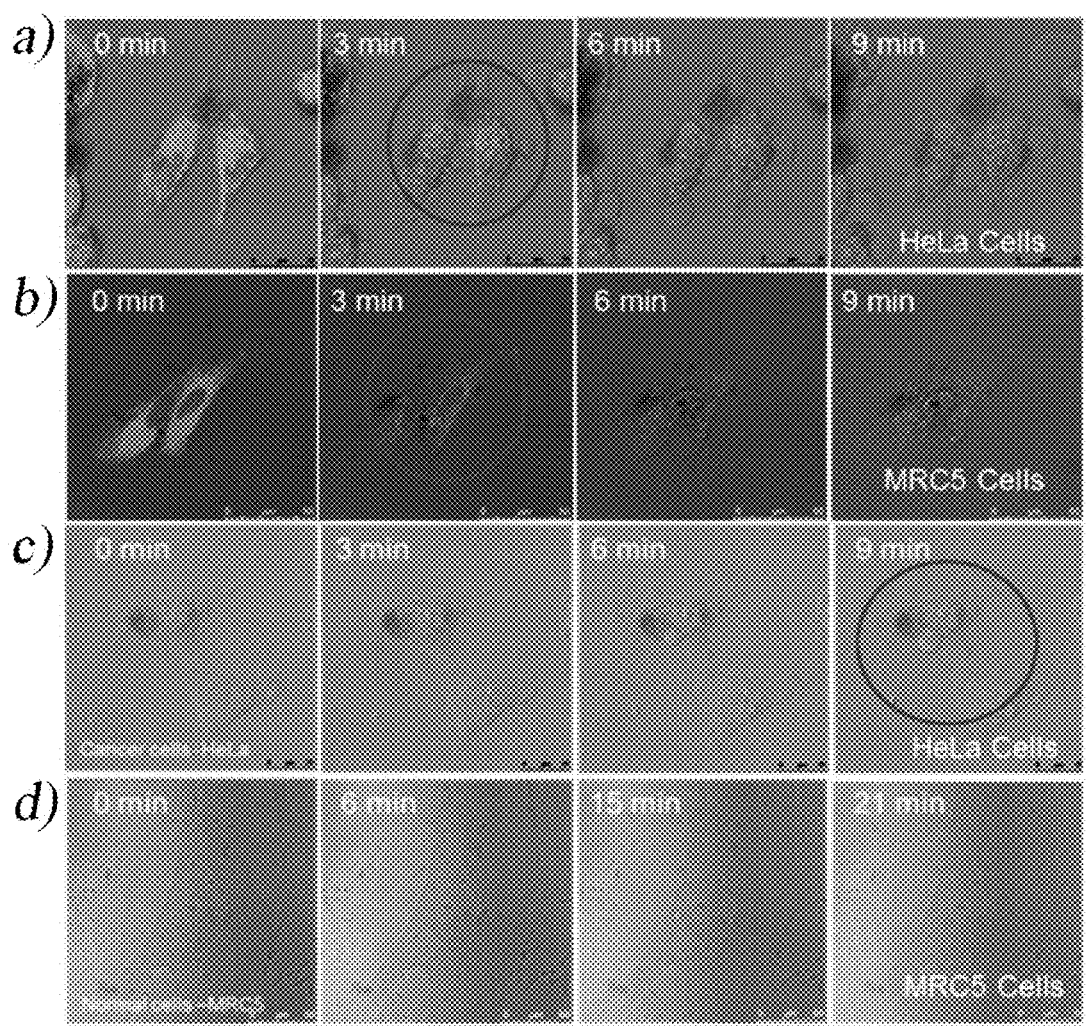
FIG. 3 shows the in vitro imaging of Gd—N and Gd—RhB in tumor cells—HeLa and normal cells—MRC5 (as the controls) after 2-hour incubation. PDT effect was triggered upon 860 nm excitation. a) Gd—RhB in HeLa; b) Gd—RhB in MRC-5; c) Gd—N in HeLa; d) Gd—N in MRC-5 (1 μM).

Investigations with relation to real PDT-applications of Gd—N in vitro and, particularly, in vivo had been accomplished in terms of tumor selectivity, cytotoxicity and photocytotoxicity, imaging, PDT efficiency, as well as biodistribution. The selectivity of Gd—N against tumor and normal cells are superiorly distinct. As shown in FIG. 1b)-d), in the HeLa cancer cell, strong red emission from the porphyrin of Gd—N can be observed on the periphery, that is, the membrane surface, after 2-hour incubation; upon incubation with more than 15 hours, several red emission can even enter and scatter internally to the cytoplasm. In the normal cell MRC-5, however, no emission can be detected on the surface of or inside the cell even after the 12 hours of incubation. In order to have a fair comparison, Gd—RhB had been synthesized for the control experiments. Rhodamine B (RhB) is a well-known mitochondria vector common for conjugation. Under the same experimental condition (incubation time, concentration, cell lines and laser power), the Applicants can find Gd-RhB's emission in both normal and cancer cells' mitochondria, and this very observation becomes the clear, cognizant, and convincing evidence of the tumor-specific property of the Gd—N. (FIG. 3) Through the MTT assays, the cytotoxicity of the three complexes, Gd—N, Yb—N and Gd—RhB in dark can be subsequently determined against the two kinds of cell lines. The $IC_{50}$ values of them are 0.78, 0.80, and 0.65 mM in cancer cells (HeLa) and 0.70, 0.70, and 0.45 mM in normal cells (MRC-5) respectively. The underlying reason of the vast difference in the dark cytotoxicity of Gd—RhB towards cancer/normal cells compared with the other two can be largely due to its non-selectivity. Again, it is the peculiarity of one embodiment of the presently invented Gd—N that can behave the crucial tumor selectivity. The in vitro PDT effect of the three complexes was evaluated using in vitro confocal microscopy and photocytotoxicity assays. Gd—N, Yb—N and Gd—RhB complexes had been dosed in HeLa cells and MRC-5 cells for 6 hours, and then subjected to excitation at 860 nm for triggering any PDT effect. (Three complexes are all available for TP-induced in vitro imaging with TP cross-section ~351 GM; given the limitation of the confocal spectroscope, the emission from porphyrin had only been monitored from 600 nm to 750 nm only) In FIG. 3, the emission of Gd—RhB can be noticed in the mitochondria. Upon suitable laser-induction, only small quantities of $^1O_2$ can be produced but the cancer cells can be killed within a few minutes; in effect, the normal cells can also be killed rapidly under the same conditions. The PDT effect of Gd—RhB is therefore efficient enough but obviously undesirable; it can accumulate inside the mitochondria of cancer and normal cells, annihilating them unselectively. Although Yb—N is cancer-specific, its incapability to produce any $^1O_2$ imposes a restriction on its any PDT practice. Surprisingly, when it comes to the red emissive Gd—N, not only can it recognize and localize on the anionic membrane of the tumor cell, but can also get access to certain parts of the cytoplasm and induce cancer apoptosis via $^1O_2$ upon 9-minutes light dose flashing 5 seconds per minute. Of course, it is very true that more time is required to trigger cancer cell deaths by Gd—N after definite laser irradiation; however, there are no significant cell deaths in the normal cells, far outweighing its slow-response drawback.

Figure 4:
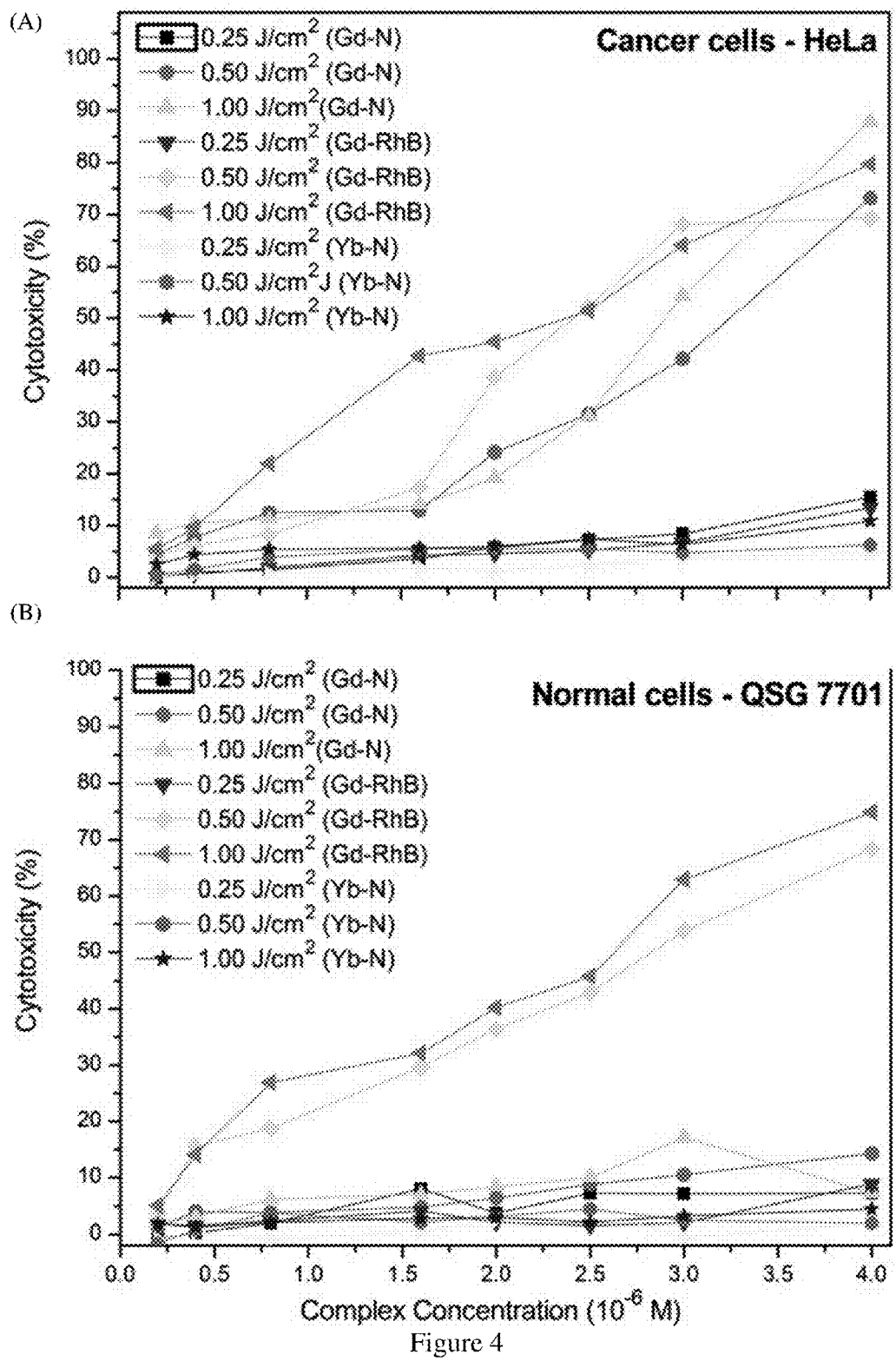
FIG. 4 shows the photocytotoxicities of Gd—N, Gd—RhB (control) and Yb—N (control) towards (A) the cancer cell (HeLa) and (B) normal cell (QSG 7701). Gd—N ($^1O_2$ available, tumor specific, strong photocytotoxicity in cancer cells, but no photocytotoxicity in normal cells), Gd—RhB (control—$^1O_2$ available, non tumor specific, strong cancer and normal cell photocytotoxicity) and Yb—N (control, $^1O_2$ not available, no photocytotoxicity in both cancer and normal cells). Photocytotoxicity curves were obtained using 1 μM of conjugates and various light doses from 0 to 1 J/cm$^2$; MTT assays were carried out after incubation for 24 hours. (37° C., 5% CO$_2$)
Figure 5:
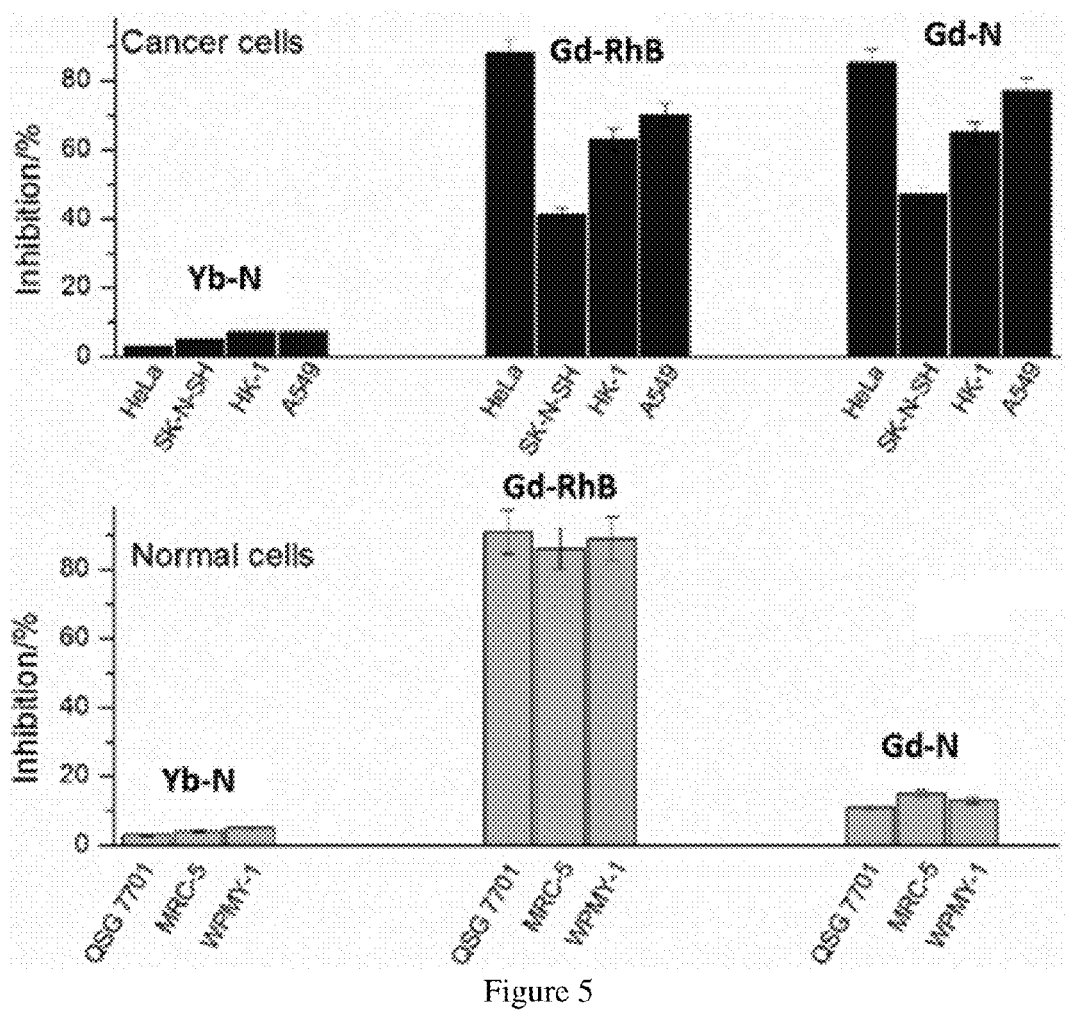
FIG. 5 shows the in vitro photocytotoxicity assays ($\lambda_{ex}$=430 nm) of the tumor-specific Gd—N in four tumor cell lines (HeLa, SK-N-SH, HK-1 and A549) and three normal cell lines (QSG 7701, MRC-5, WPMY-1), as well as the two controls—Yb—N and Gd—RhB.

As any new-generation PDT agent, the concentration-dependent photocytotoxicity of Gd—N, Yb—N and Gd—RhB, ranging from 0.2 to 1 μM dosage, had also been measured under varying light doses from 0.25 to 1 J/cm$^2$ in cancer cells and normal cells. The light dose-response curves obtained are displayed in FIG. 4A. In the HeLa cancer cells, Gd—RhB and Gd—N have exhibited strong photocytotoxicity, whereas Yb—N (without singlet oxygen) has no photocytotoxicity. From FIG. 4B, in the normal cell QSG 7701, no photocytotoxicity can be found from Gd—N, while Gd—RhB gives very similar results as it behaved in the cancer cells. Such trend does seem to correlate with the selective cellular uptake of Gd—N by the cancer and normal cells. The Applicants had extended the studies with the use of more cancer cell and normal cell lines, and the results are shown in FIG. 5—Gd—N can maintain its good tumor selectivity towards total of 7 cell lines (four cancer cells and three normal cells), thereby acting as an outstanding and specific PDT agent.

Figure 6:
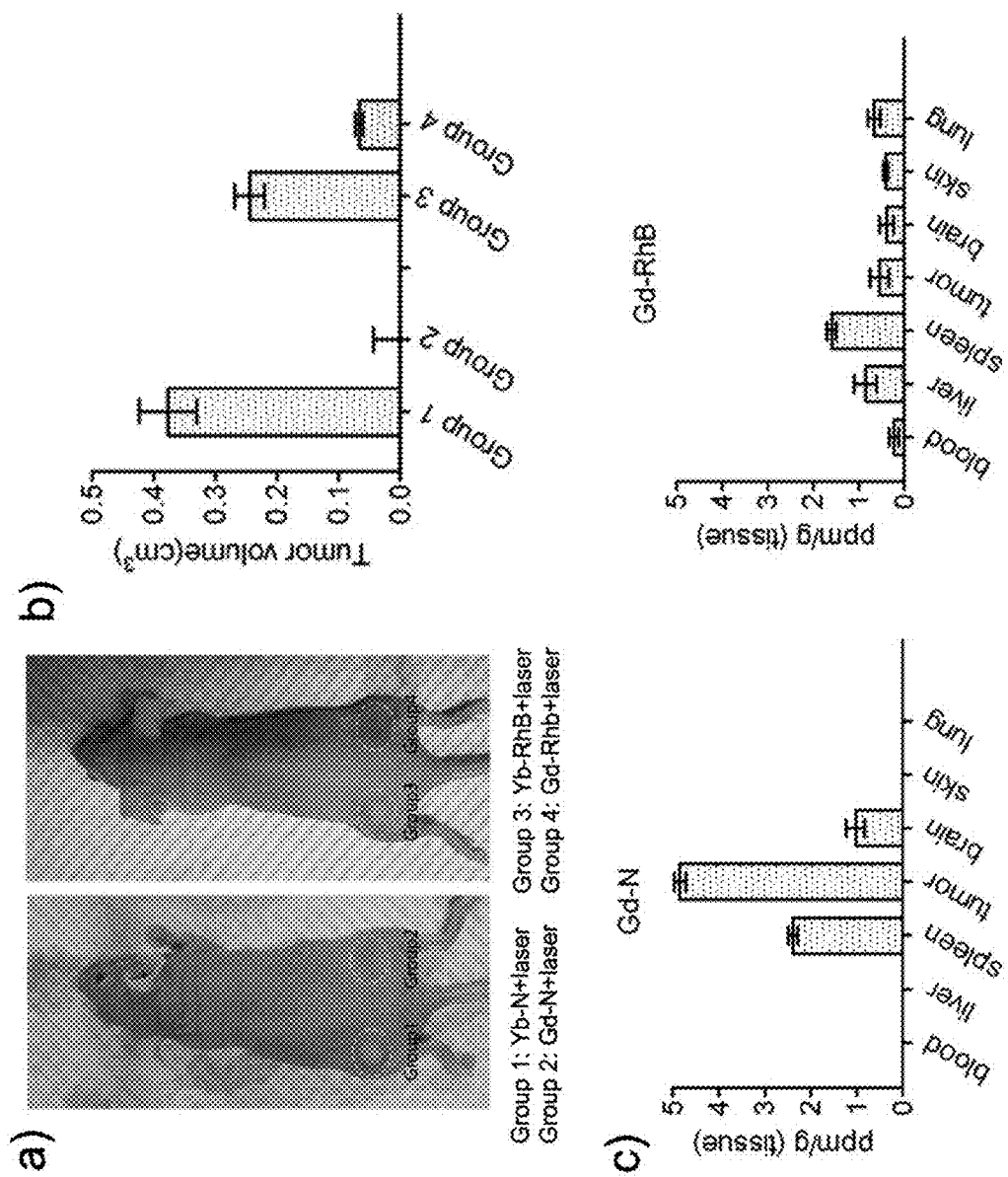
FIG. 6 shows in vivo studies of Gd—N as the cancer cell-specific PDT agent. a) The representative gross images of tumors after PDT using 860 nm laser for excitation, and candidates were divided into four groups (Group 1: Yb—N; Group 2: Gd—N; Group 3: Yb—RhB; Group 4: Gd—RhB); b) the measurement of tumor volume in a); c) In vivo biodistribution of Gd—N via ICP-MS studies; d) Two-photon microscopic images of tumor samples in c); e) In vivo tumor inhibition assays of Gd—N; f) In vivo tumor inhibition via Gd—N induced $^1O_2$ through caudal vein injection.
Figure 6:
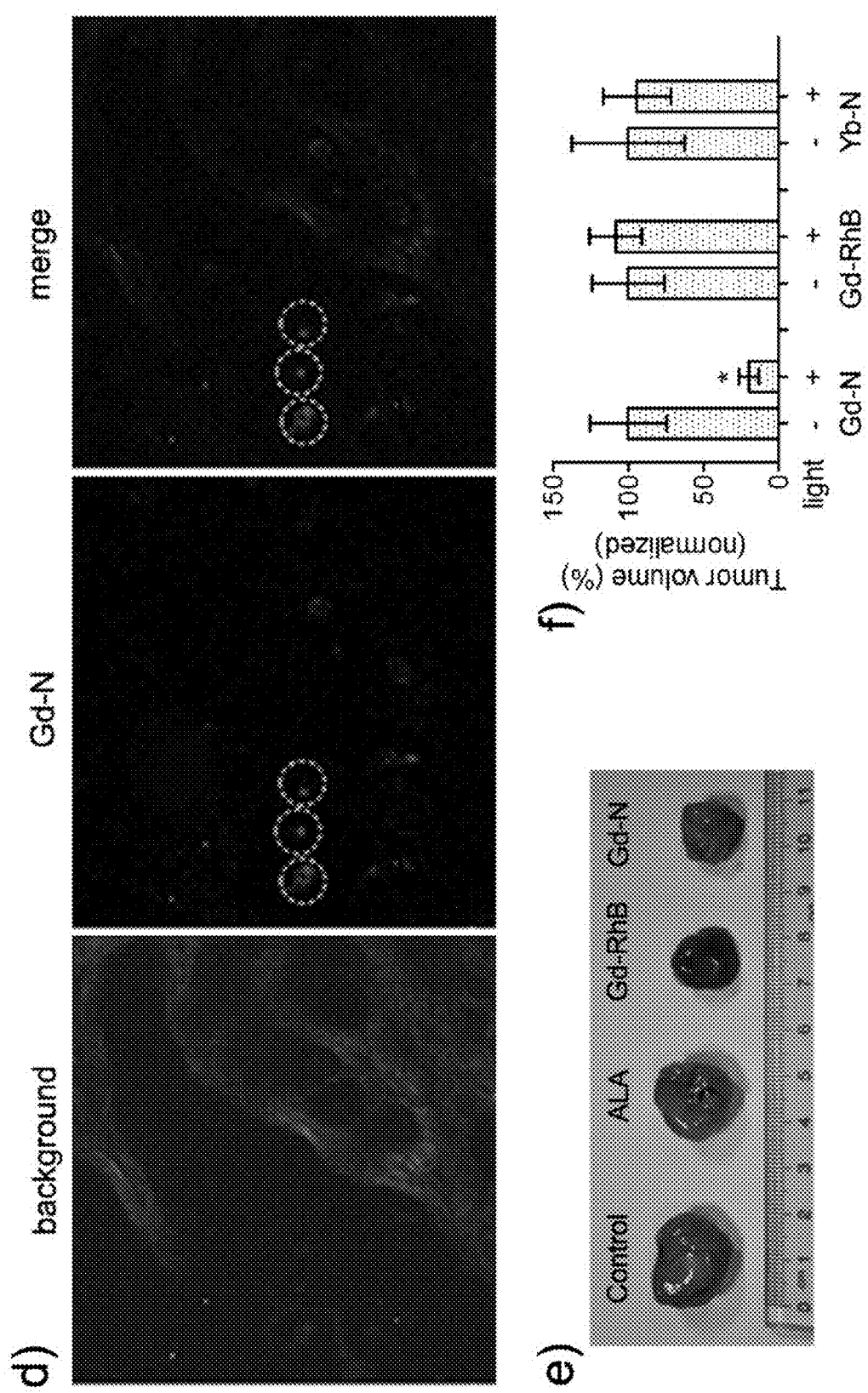

To understand more about the in vivo uptakes of the presently invented complexes, studies of biodistribution on these complexes' specialty towards particular organs infections had been carried out via xenograft mouse models and ICP-MS. In the first proof-of-concept experiment, the four complexes had been classified into four groups. HeLa cells pre-incubated separately with Gd—N, Yb—N, Gd—RhB and Yb—RhB were subcutaneously injected into BALB/c nude mice and then irradiated the injected sites with 860 nm laser. Two weeks later, mice were pictured and the tumor volumes were measured (where the picture of the mice and measurement of tumor volumes are shown in FIGS. 6a and 6b, respectively) and the tumors were found much effectively inhibited in the groups of Gd—N and Gd—RhB, compared with their counterparts Yb—N and Yb—RhB; Gd—N, among the four complexes, is the best in vivo PDT agent that can devastate the tumor with 100% efficiency. Biodistribution study-wise, BALB/c nude mice with tumor xenograft attaining a size of approximately 0.1 cm$^3$ were caudal vein injected with Gd—N (1.0 mg/kg). Two days after the chemical administration, the concentrations in different tissues or circulating blood were examined using ICP-MS. It is shown in FIG. 6c that tumors have the largest enrichment of Gd—N (4.84 ppm/g), suggesting the specific recognition of the Gd—N towards tumor cells.

This result was also confirmed by two-photon microscopic imaging of the tumor tissues extracted from Gd—N administrated BALB/c nude mice. There are obvious two-photon microscopic signal from Gd—N (image of Gd—N, circled points), while the control image (showed as background, imaged by bright field) showed no specific signal. The merge image is the overlap photon of Background and Gd—N which is shown FIG. 6d. Further verification of the inhibiting effect of Gd—N and Gd—RhB towards tumor growth in tumor-bearing mice was done by intratumorally injecting BALB/c nude mice of HeLa xenograft tumor of approximately 0.3 cm$^3$ with respectively Gd—N (2.0 mg/kg), Gd—RhB (2.0 mg/kg) and ALA (60 mg/kg) (5-aminolevulinic acid, which can produce protoporphyrin in living cells and herein serve as the control PDT chemical), and irradiating with 860 nm light for three hours after complex injection. The total light dosage to tumor was 50 J/cm$^2$.

Tumors were then allowed for growth for another 7 days and subjected for final extraction and picturing. As shown in FIG. 6e, the outcomes of these studies do constitute that Gd—N is capable of tremendously inhibiting and even reducing the size of solid tumor by half from 2 cm to 1 cm within a short period of time.

Alternatively, mice with xenograft tumor were caudal vein injected with Gd—N and Gd—RhB (2.0 mg/kg body weight) and allowed for full circulation for 6 hours. Then tumors were irradiated with 860 nm light similarly as above. The tumor on the opposite side served as the control (light untreated). The treatments were repeated for three times in the following days in a one-time-per-day manner. Consistently, it was found that Gd—N plus light treated tumors were inhibited compared to their opposite flank controls of tumor or Gd—RhB groups. Pharmacokinetics analyses showed also that Gd—N persisted in animals for a longer time with a larger MRT (mean resistance time) value (12.50 hours), while Gd—RhB was fast cleared (with MRT of 5.04 hours) (results are illustrated in FIG. 6f and Table 1).

TABLE 1

Pharmacokinetic parameters of Gd—N and Gd—RhB in plasma after caudal vein injections of 20 nmol of Gd—N (37.34 μg) or Gd—RhB (44.28 μg) to BALB/c nude mice (n = 3), respectively.

| Parameters | Gd—N | Gd—RhB |
| --- | --- | --- |
| Equation | $C_{(t)} = 138.61\ e^{-0.08t}$ | $C_{(t)} = 176.08\ e^{-0.1986t}$ |
| AUC$_{(0-t)}$ (μg/mL × h) | 1732.63 | 886.61 |
| MRT$_{(0-t)}$ (h) | 12.50 | 5.04 |
| t$_{1/2}$ (h) | 8.66 | 3.49 |
| V$_d$ (mL) | 0.269 | 0.251 |

AUC, area under the concentration-time curve; MRT, mean residence time; t$_{1/2}$, statistical half life; V$_d$, volume of distribution.

Figure 7:
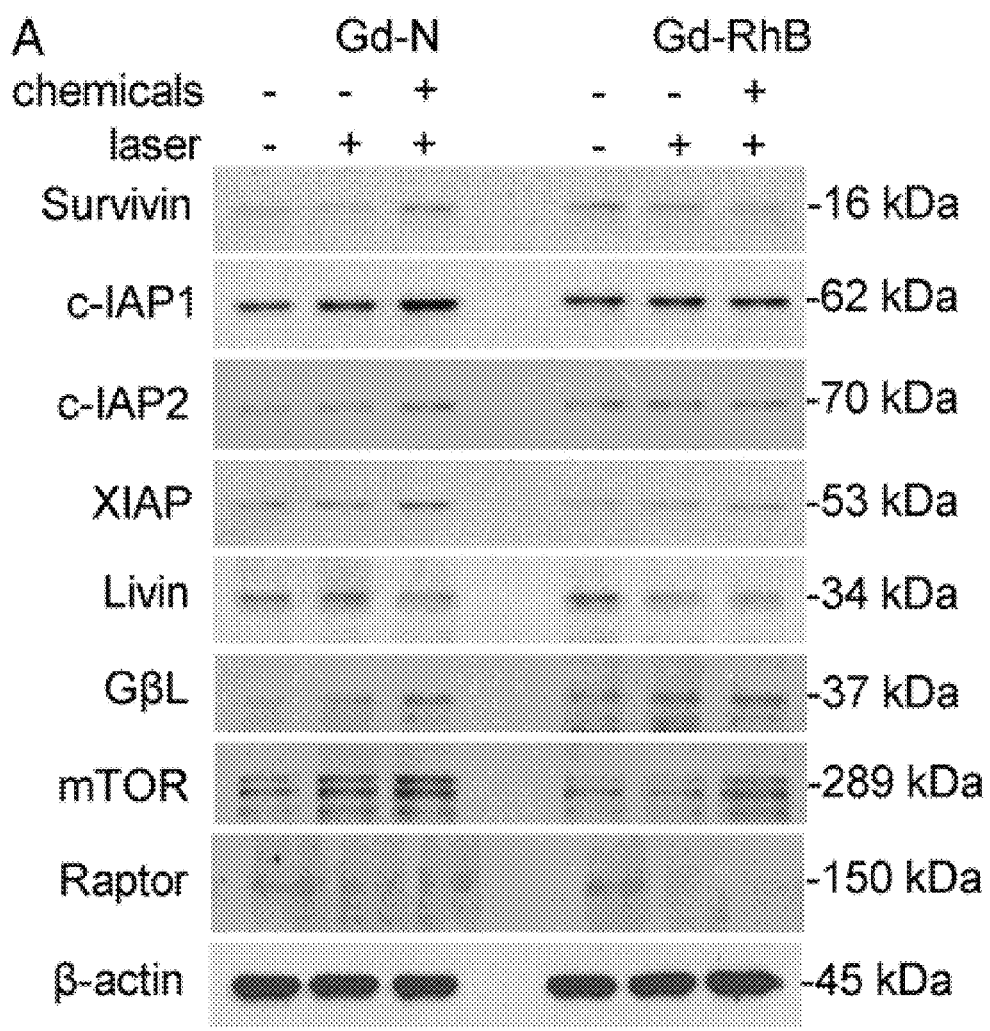
FIG. 7 shows Gd—N and Gd—RhB induced $^1O_2$ activated the inhibitor of apoptosis protein family and mTOR pathway. A—HeLa cells dosed with 1 μM Gd—N or Gd—RhB and irradiated with 0.5 J/cm$^2$ were harvested for western blotting. Untreated or free of chemicals samples were served as the controls. B—Cellular protein changes were semi-quantitatively measured using Gel-Pro Analyzer software of western blotting bands in A and showed as the ratio to β-actin (loading control of total proteins). P values were calculated between untreated and Gd—N or Gd—RhB plus laser groups by One-way Analysis of Variance.
Figure 7:
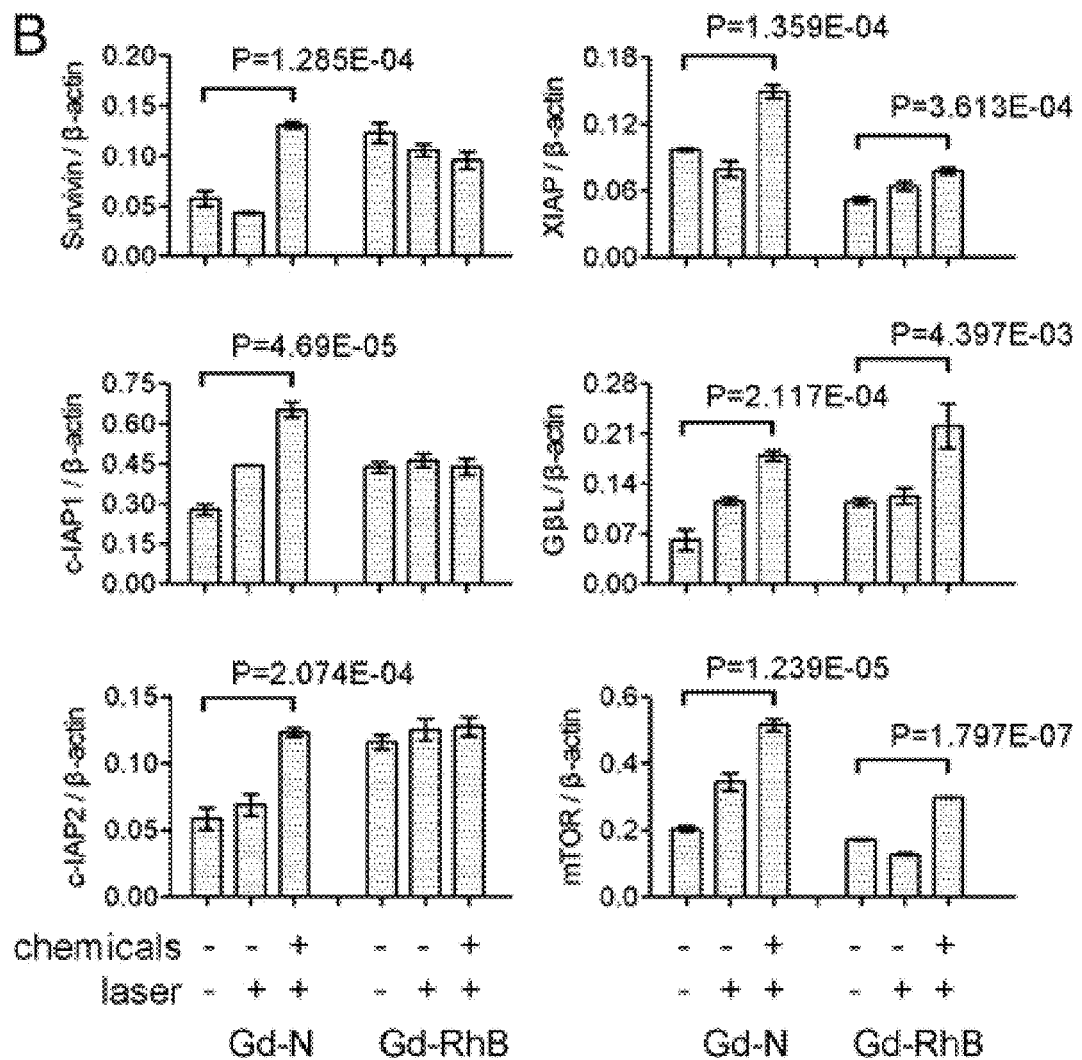

In regard to the molecular mechanism of PDT, the protein levels of cellular survivin and inhibitors of apoptosis protein family (IAP) in protein lysates of PDT-treated HeLa cells were also investigated. As proposed, survivin and the IAP family members, c-IAP1, c-IAP2 and XIAP, were all remarkably expressed in Gd—N plus laser-treated samples. Besides, it is rather surprising to find that mTOR pathway may be involved in response to the PDT treatment of the cancer cells. The levels of two critical members, mTOR and GβL, were obviously elevated upon Gd—N or Gd—RhB induced $^1O_2$ stress stimulus. These results demonstrate the successful cell killing effect of Gd—N promoted photodynamic therapy at the molecular level and may also shed new light on the design and improvement of current PDT agents. (FIG. 7)

Conclusion

The present invention provides theranostic gadolinium complex Gd—N for use as an anti-cancer torpedo which is equipped with visible-to-NIR emission for imaging, tumor cell selectivity, and $^1O_2$ generation. Through a string of in vitro and in vivo studies, it is found that the effectiveness and advantages of the presently present Gd—N had been adequately corroborated and demonstrated that the present Gd—N to be the next-generation smart dual-functional PDT agent. One embodiment of the present invention is method of tracking and imaging long-term live cancer cell, using the present Gd—N, as well as selective photodynamic therapy.

Experimentation Methods

Linear Induced Photophysical Properties

The Applicants had recorded the UV-Visible absorption spectra (ranging from 200 to 1100 nm) and single-photon luminescence spectra of all presently invented complexes with, respectively, an HP UV-8453 spectrophotometer and an Edinburgh Instrument FLS920 Combined Fluorescence Lifetime and Steady state spectrophotometer equipped with a UV-to-NIR-sensitive photomultiplier inside a nitrogen flow cooled housing. The Applicants had corrected all the spectra from the detector response and stray background light phosphorescence, measuring the quantum yields of the lanthanide complexes by a demountable 142 mm (inner) diameter barium sulphide-coated integrating sphere supplied with the two access ports in Edinburgh Instrument FLS920.

Singlet Oxygen Quantum Yield

With the phosphorescence at 1270 nm, the Applicants had detected the singlet oxygen with an InGaAs detector on the PTI QM4 luminescence spectrometer, and determined the quantum yields ($\Phi_\Delta$) of all compounds in $CHCl_3$ through comparing the $^1O_2$ emission intensity of the sample solution to that of a reference material[4] ($H_2TPP$, $\Phi_\Delta$=0.55 in $CHCl_3$) as illustrated in the following equation:

$$\Phi_\Delta^S = \Phi_\Delta^{REF} \times \left(\frac{n_S}{n_{REF}}\right)^2 \frac{G_\Delta^S}{G_\Delta^{REF}} \times \frac{A_{REF}}{A_S}$$

where $\Phi_\Delta$ denotes the singlet oxygen quantum yield, $G_\Delta$ indicates the integrated emission intensity, A represents the absorbance at the operation excitation wavelength, n reflects the solvent's refractive index, given that the Superscripts REF and S stand for the reference and sample respectively. In all cases, the Applicants had measured the $^1O_2$ emission spectra upon due excitation. To reduce the impacts of re-absorption of the emitted light, all absorbance were set at 0.05 as well.

Cell Culture

Human HeLa (cervical carcinoma) and WPMY-1 (normal prostate stroma immortalized cell) cells were grown in DMEM medium; A549 (lung adenoma) were maintained in a mixture of Ham's F12K medium and L-glutamine (N3520, Sigma, St. Louis, Mo., USA); QSG 7701 (normal liver cell), HK-1, HONE1 (nasopharyngeal carcinoma) were grown in RMPI-1640 medium; MRC-5 (normal lung fibroblasts) and SK-N-SH (neuroblastoma) cells were grown in MEM medium. What were added also is (i) 10% (v/v) fetal bovine serum (FBS), (ii) 100 μg/ml streptomycin, and (iii) 100 units/ml penicillin.

In Vitro Imaging

To test the suitability of the presently invented water-soluble complexes as bioprobes, the Applicants had, using a commercial confocal laser scanning microscope, Leica TCS SP5, equipped with a Ti: Sapphire laser (Libra II, Coherent) as well as a 980 nm wavelength laser for excitation, conducted in vitro imaging of HeLa/WPMY-1/MRC-5 cells with which the presently invented five complexes was incubated.

MTT Cell Viability Assay.

After 24 hours, the water-soluble complexes and the targeted cells treated were incubated further with 3-(4,5-dimethylthiazol-2-yl)-2,5-diphenyltetrazolium bromide (0.5 mg/ml), otherwise known as MTT, for 4 hours, so that formazan can be formed along with the cell's metabolic pathways. Then, the Applicants had extracted the formazan and dissolved it by dimethyl sulfoxide (DMSO), with the absorbance of the subsequent solutions being measured in a Bio-Rad iMark microplate reader (490 nm). Quadruplicates were performed and the Applicants had interpreted and analyzed the data by plottings using the GraphPad Prism 5 software.

Photodynamic Treatment (PDT) Assay

On the 96-well plate, cancer cells ($2\times10^4$/well) were first incubated overnight and then treated with the presently invented complexes and control analogues for the next 6 hours in dark. After the old medium being replaced with the fresh one, the cells were accordingly exposed to yellow light (1-8 $J/cm^2$) generated from a 400 W tungsten lamp fitted with a heat-isolation filter and a 500 nm long-pass filter under the fluency rate of mW/cm2. After that, the Applicants had examined the post-PDT cell viability by the MTT assay after 24 hours. The Applicants had rinsed the cell monolayers with PBS prior to incubation with 250 μg/mL MTT solution at 37° C. for 3 hours. The formazan crystals formed and dissolved in DMSO then underwent absorbance measurement at 540 and 690 nm by a 96-well plate reader (ELx800 Absorbance Microplate Reader).

Animals:

The Applicants had done all the experiments entailing animal models on the athymic nude mice (BALB/c-nu/nu) which were all obtained from Guangdong Medical Lab Animal Center (license number: SCXK-2008-0002). Mice were raised and operated according to the strict protocol the National Standard of Animal Care and Use Procedures (20080820).

Pharmacokinetics Analysis:

Gd—N and Gd—RhB (1.0 μmol/kg body weight each) were caudal vein injected into the mice. Then sera were collected at different time points from 0-20 hours as indicated. The concentrations of Gd—N and Gd—RhB were measured by PerkinElmer EnVision Multilabel Reader 2104 at 570 nm, and calculated using standard absorptions via concentration curve. Pharmacokinetic parameters ($t_{1/2}$, Vd, MRT, AUC) were calculated by fitting with one compartment model.

In Vivo Bio Distribution Via ICP-MS

To understand more about the in vivo uptakes of the presently invented complexes in biodistribution studies with complexes' specialty to particular organs/bacterial infections are to be carried out via ICP-MS. The Applicants administer Gd—N and Gd-PhB to the mice at a dosage of 1.0 μmol/kg body weight when they found that tumor xenograft had attained a size of 0.1 $cm^3$ approximately. When two days passed, around 0.02-0.04 gram of sample tissues were collected in tumor, liver, lung, kidney, spleen, brain, prostate, and skin; blood (80-90 μL) is also no exception. The Applicants had incubated all samples with 500 μL nitric acid at 37° C. for releasing the metal ions for further ICP-MS examinations, in addition to dissolving the interfering organic molecules.

In Vivo Photodynamic Therapy Studies

For the establishment of the mouse tumor xenograft mode, cells were to be trypsinized, harvested and suspended in the culture medium. The Applicants had injected $1\times10^6$ cells in 100 μL volume s.c. into the flanks of female athymic nude mice (with 5-week old) and waited for 10-15 days. When the tumor volume reached the size of 100-150 $mm^3$, the Applicants divided the animals randomly into different groups for further experiments. Tumor volume was measured by calipers (accuracy of 0.02 mm) and then calculated independently on the basis of the equation $V=(L \times W^2)/2$, where L and W correspond to the larger and smaller dimensions respectively. One-way analysis of variance towards statistical significances between groups was assessed by the GraphPad Prism 5.0 software.

Materials and Methods

All chemicals used were of reagent-grade and were purchased from Sigma-Aldrich and used without further purification. Preparations of intermediates $Yb[N(SiMe_3)_2]_3$. $[LiCl(THF)_3]$[1] and starting porphyrin free base TFP-TMS[2] were performed according to the literature procedures.[3] Preparations of the control compound Gd—RhB, Yb—RhB[4] and Yb—N[5] were accomplished according to the inventors' previous procedures, respectively. All analytical-grade solvents were dried by standard procedures, distilled and deaerated before use. High-resolution mass spectra, reported as m/z, were obtained on a Bruker Autoflex MALDI-TOF mass spectrometer. Elemental analyses carried out at the School of Chemical Engineering, Northwest University, P. R. China. The synthetic route of intermediates and Gd—N was shown in the Scheme 1:

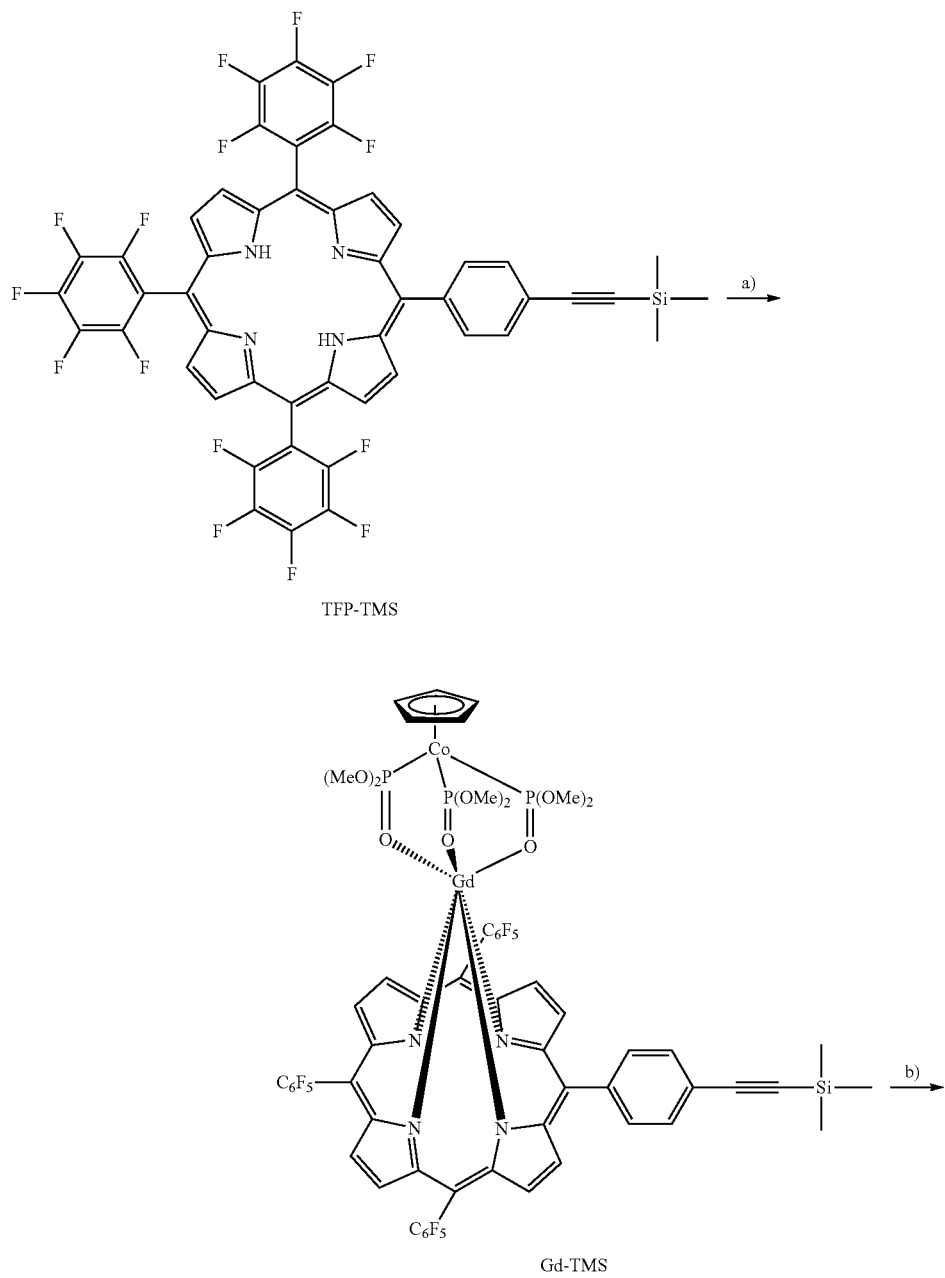

Scheme 1.

-continued
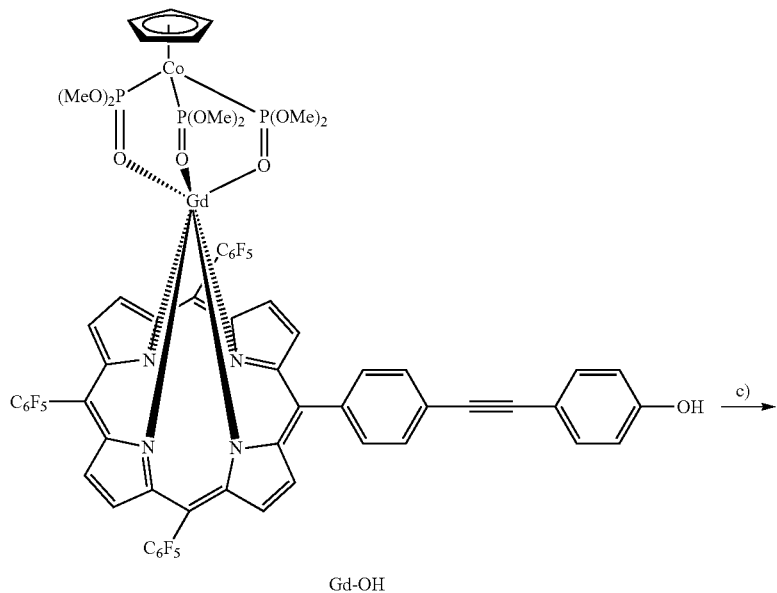
Gd-OH
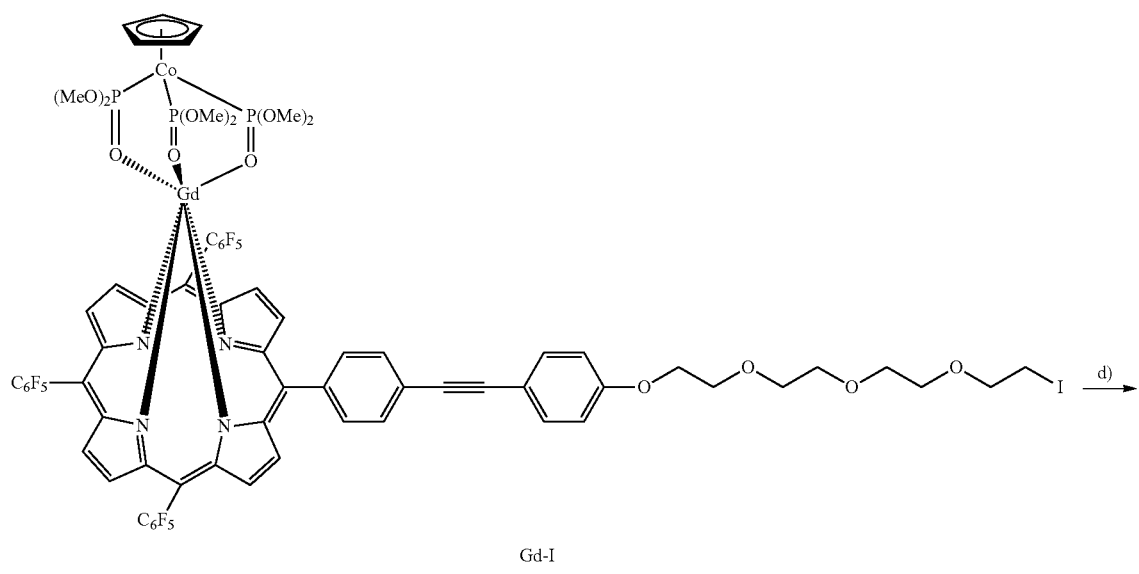
Gd-I

-continued

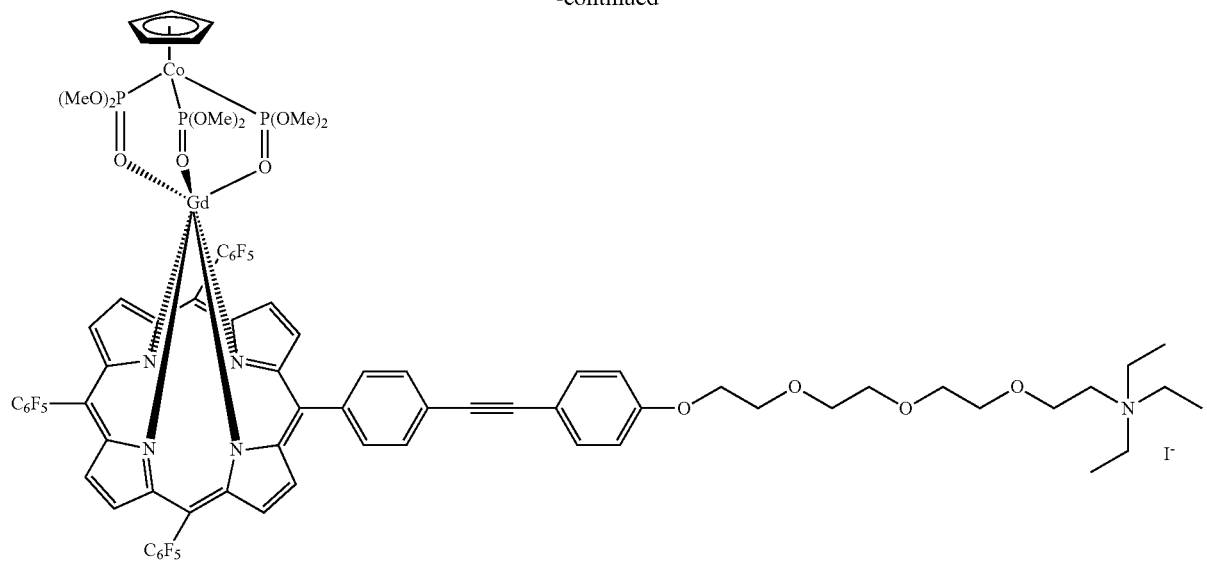

Gd-N a) (i) Gd[N(SiMe$_3$)$_2$]$_3$·[LiCl(THF)$_3$]$_x$, toluene, reflux, 12 h; (ii) Na{(η$^5$-C$_5$H$_5$)Co[P(=O)(OMe)$_2$]$_3$}, toluene, rt, 1 h; b) (i) TBAF, (THF, 1M), CH$_2$Cl$_2$, rt, 30 min; (ii) a) 4-iodophenol, Pd(PPh$_3$)$_4$, CuI, THF, NEt$_3$, 40° C., 12 h; c) Tetraethyleneglycol diiodide, DMF, K$_2$CO$_3$, 80° C., 8 h; d) Triethylamine, DMF, 85° C., 24 h.

The synthetic routes of Gd—NGd-TMS: A solution of Gd[N(SiMe$_3$)$_2$]$_3$·[Li(THF)$_3$Cl]$_x$ (5.0 ml, 0.6 mmol Gd) was transferred to a Schlenk flask and the solvent was removed under vacuum. Then 10 ml dichloromethane (CH$_2$Cl$_2$) was added for the precipitation of LiCl. The mixture was centrifuged and the clear layer was transferred to another Schlenk flask with the porphyrin free base TFP-TMS (196 mg, 0.2 mmol) dissolved in 20 ml toluene. The resulting solution was refluxed for 12 hours until most of the free base are coordinated with the metal ion. The reaction solution was cooled to room temperature. Then dry Na{(η$^5$-C$_5$H$_5$)Co[P(=O)(OMe)$_2$]$_3$} (104 mg 0.22 mmol) was added to the mixture which was magnetically stirred for another 1 hour. After the reaction was complete, the solvent was removed under vacuum and the residue dissolved in CH$_2$Cl$_2$, filtered and chromatographed on silica gel using CH$_2$Cl$_2$/Hexane as eluent to afford the pure product as a red solid. Yield: 86%; MALDI-TOF MS: calcd. for [M$^+$]: M. p.>300° C.; 1587.1965. found: 1587.2154. Anal. Calc. for [C$_{60}$H$_{44}$CoF$_{15}$N$_4$O$_9$P$_3$SiGd]: C, 45.40; H, 2.79; N, 3.53%. Found: C, 45.46; H, 2.83; N, 3.51%; UV/Vis (DMSO, 25° C.): λ$_{max}$(log ε)=427 (5.68), 558 (4.34), 597 (3.29 dm$^3$ mol$^{-1}$ cm$^{-1}$).

Gd—OH:

Tetrabutylammonium fluoride (TBAF, 1.0 M in THF, 200 μL, 0.2 mmol) was added to a solution of Gd-TMS (182 mg, 0.1 mmol) in 10 ml CH$_2$Cl$_2$, and the solution was stirred for 30 minutes. The progress of the reaction was monitored by TLC. After completion of the reaction, the mixture was passed through a short column of silica gel. After removal of the solvent, the intermediate was obtained and used for the next step without further purification. Then the obtained intermediate and 4-iodophenol (33 mg, 0.15 mmol) were dissolved in dry tetrahydrofuran (THF, 15 ml) and triethylamine (NEt$_3$, 5 mL), and the mixture was bubbled with nitrogen for 30 minutes. After that, Pd(PPh$_3$)$_4$ (12 mg 0.01 mmol) and CuI (3.8 mg, 0.02 mmol) were added to the above solution. The reaction mixture was stirred at least 35° C. for at least 10 hours under a nitrogen atmosphere. Then the solvent was removed under reduced pressure. The residue was purified by column chromatography on silica gel using CH$_2$Cl$_2$/Methanol (50:1) as eluent to afford the pure product as a red solid. Yield: 73% (Table 2); M. p.>300° C.; MALDI-TOF MS: calcd. for [M$^+$]: 1607.0291. found: 1608.0308. Anal. Calc. for [C$_{63}$H$_{40}$CoF$_{15}$N$_4$O$_{10}$P$_3$Gd]: C, 47.08; H, 2.51; N, 3.49%. Found: C, 47.10; H, 2.49; N, 3.51%; UV/Vis (DMSO, 25° C.): λ$_{max}$ (log ε)=426 (5.70), 555 nm (4.48 dm$^3$ mol$^{-1}$ cm$^{-1}$).

TABLE 2

Yield in different cross-coupling reaction condition(%).

| Temperature (° C.) | Time (hours) | | |
| --- | --- | --- | --- |
| | 10 | 12 | 15 |
| 35 | 60 | 64 | 69 |
| 40 | 68 | 73 | 74 |
| 60 | 59 | 62 | 66 |

Considering both time and temprature, 40° C. and 12 hours was selected as the major reaction condition.

Gd—I:

To a solution of Gd—OH (161 mg, 0.1 mmol) and tetraethyleneglycol diiodide (207 mg, 0.5 mmol) in dry N,N-Dimethylmethanamide (DMF, 10 ml) was added anhydrous K$_2$CO$_3$ (69 mg, 0.5 mmol), and the mixture was heated to 80° C. for 8 hours under a nitrogen atmosphere. Then the solvent was removed under reduced pressure. The crude product was purified by column chromatography on silica gel eluented by CH$_2$Cl$_2$/CH$_3$OH (v/v, 100:1) to afford the pure product as a red solid. Yield: 82%; M. p.>300° C.; MALDI-TOF MS: calcd. for [M$^+$]: 1893.2210. found 1893.1038. Anal. Calc. for [C$_{71}$H$_{55}$CoF$_{15}$IN$_4$O$_{13}$P$_3$Gd]: C, 45.04; H, 2.94; N, 3.11%. Found: C, 45.21; H, 2.99; N, 3.06%; UV/Vis (DMSO, 25° C.): λ$_{max}$ (log ε)=425 (5.71), 555 nm (4.50 dm$^3$ mol$^{-1}$ cm$^{-1}$).

Gd—N:

To a solution of Gd—I (95 mg, 0.05 mmol) in dry (DMF, 10 ml), anhydrous NEt$_3$ (1 ml, excess) was added, and the mixture was heated to 85° C. for 24 h under the nitrogen atmosphere. Then the solvent was removed under reduced pressure. The obtained crude product was purified by silica gel column chromatography using $CH_2Cl_2/CH_3OH$ (v/v, 80:1) as the eluent to remove unreacted Gd—I and other impurities, then using $CH_2Cl_2/CH_3OH$ (v/v, 10:1) to obtain the pure product as a red solid. Yield: 80%; M. p.>300° C.; MALDI-TOF MS: calcd. for [M$^+$]: 1867.5095. found 1867.2538. Anal. Calc. for [$C_{99}H_{85}CoF_{15}N_6O_{16}P_3Gd$]: C, 46.37; H, 3.54; N, 3.51%. Found: C, 46.40; H, 3.59; N, 3.48%; UV/Vis (DMSO, 25° C.): $\lambda_{max}$ (log $\epsilon$)=426 (5.74), 555 nm (4.53 dm$^3$ mol$^{-1}$ cm$^{-1}$).

Two-Photon-Absorption Measurements

The two-photon-absorption spectra (i.e., Z-scan traces) were measured at 800 nm by the open-aperture Z-scan method using 100 fs laser pulses with a peak power of 276 GWcm$^{-2}$ from an optical parametric amplifier operating at a repetition rate of 1 kHz generated from a Ti:sapphire regenerative amplifier system. The laser beam was split into two parts by a beam splitter. One was monitored by a photodiode (D1) as the incident intensity reference, $I_0$, and the other was detected as the transmitted intensity by another photodiode (D2). After passing through a lens with f=20 cm, the laser beam was focused and passed through a quartz cell. The position of the sample cell, z, was moved along the direction of the laser beam (z axis) by a computer-controlled translatable table so that the local power density within the sample cell could be changed under the constant incident intensity laser power level. Finally, the transmitted intensity from the sample cell was detected by the photodiode D2. The photodiode D2 was interfaced to a computer for signal acquisition and averaging. Each transmitted intensity datum represents the average of over 100 measurements. Assuming a Gaussian beam profile, the nonlinear absorption coefficient, $\beta$, can be obtained by curve-fitting to the observed open-aperture traces, T(z), with Equation (1)$^6$, where $a_0$ is the linear absorption coefficient, l is the sample length (the 1 mm quartz cell) and $z_0$ is the diffraction length of the incident beam. After obtaining the nonlinear absorption coefficient, $\beta$, the 2PA cross-section, $\sigma^{(2)}$, of the sample molecule (in units of 1 GM=10$^{-50}$ cm$^4$ sphoton$^{-1}$) can be determined by using Equation (2), where $N_A$ is Avogadro's constant, d is the concentration of the sample compound in solution, h is Planck's constant and v is the frequency of the incident laser beam.

$$T(z) = 1 - \frac{\beta I_0(1 - e^{-a_0 l})}{2a_0(1 + (z/z_0))^2} \quad (1)$$

$$\sigma_2 = \frac{1000\beta h\nu}{N_A d} \quad (2)$$

INDUSTRIAL APPLICABILITY

The present invention discloses a new modality of photodynamic therapy (PDT) through the design of the present invention's truly dual-functional—PDT and imaging—gadolinium complex (Gd—N), which can target cancer, cells specifically. In one embodiment of the present invention, there is provided a PDT drug that can specifically localize on the anionic cell membrane of cancer cells in which its laser-excited photoemission signal can be monitored without triggering the phototoxic generation of reactive oxygen species—singlet oxygen—prior to due excitation. Comprehensive in vitro and in vivo studies had been conducted for the substantiation of the effectiveness of Gd—N as such a new tumor selective PDT photosensitizer modality for anticancer therapy.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

What we claim:

1. A composition for photodynamic therapy and imaging of cancer cells comprising gadolinium complex with a molecular formula of:

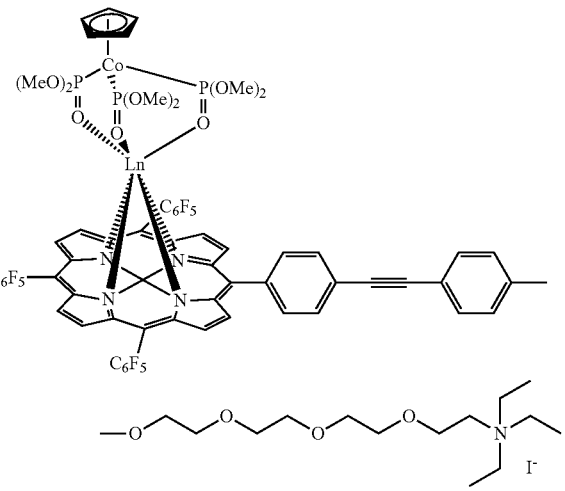

wherein Ln is Gd or gadolinium porphyrinate (Gd—N) or a pharmaceutically acceptable salt thereof.

2. The composition according to claim 1 wherein the cancer cells have anionic cell membranes.

3. A method of photodynamic therapy and imaging of cancer cells comprising administering to a subject in need thereof the composition according to claim 1 and irradiating the cancer cells in the subject in need thereof with a radiation source.

4. The method according to claim 3 wherein the administration of said composition is performed intravenously or by injection to site of said cancer cells.

5. The method according to claim 3, wherein said radiation source is a light source of about 860 nm in wavelength.

6. A method of synthesizing the composition according to claim 1 comprising steps according to the following scheme:

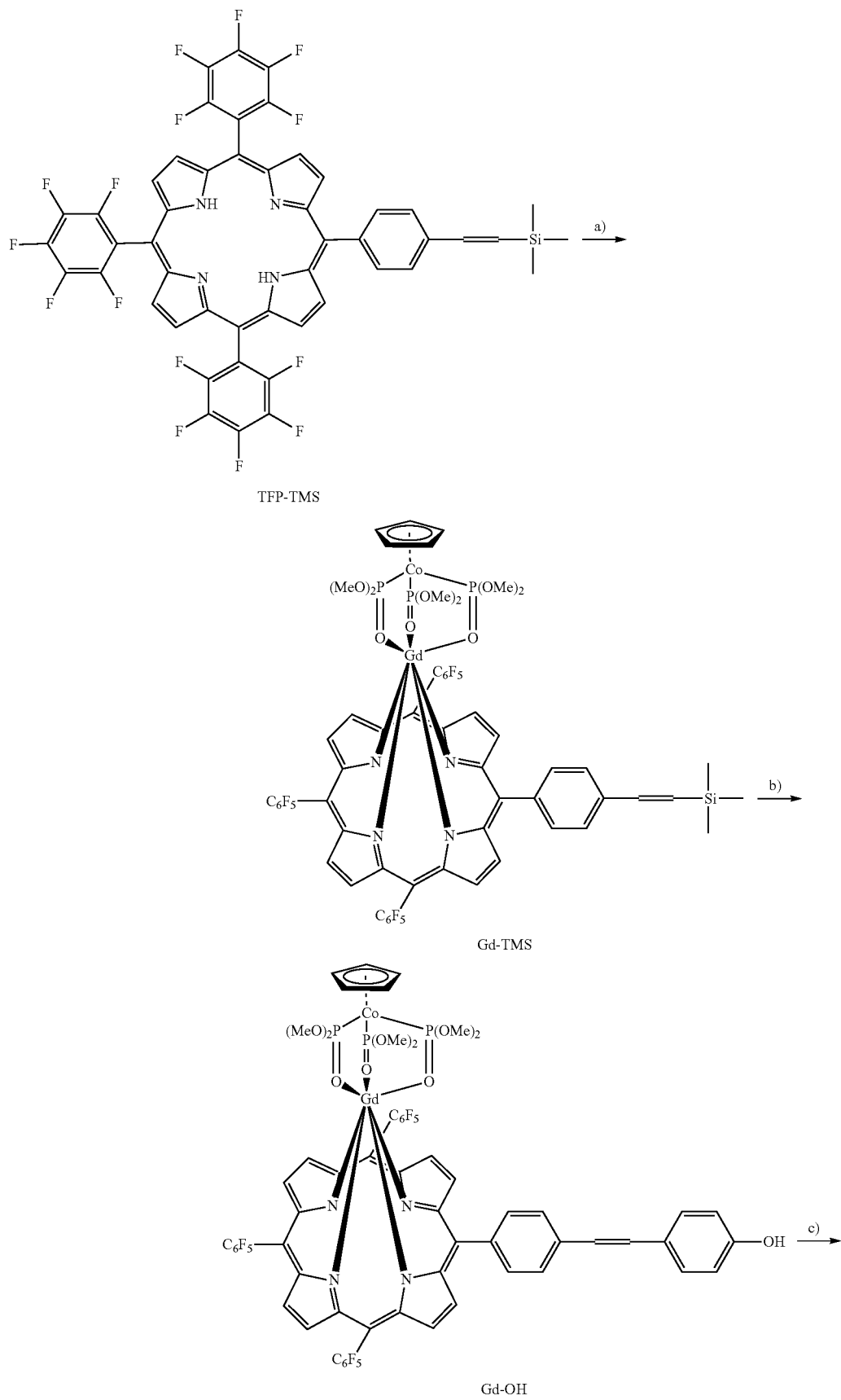

-continued

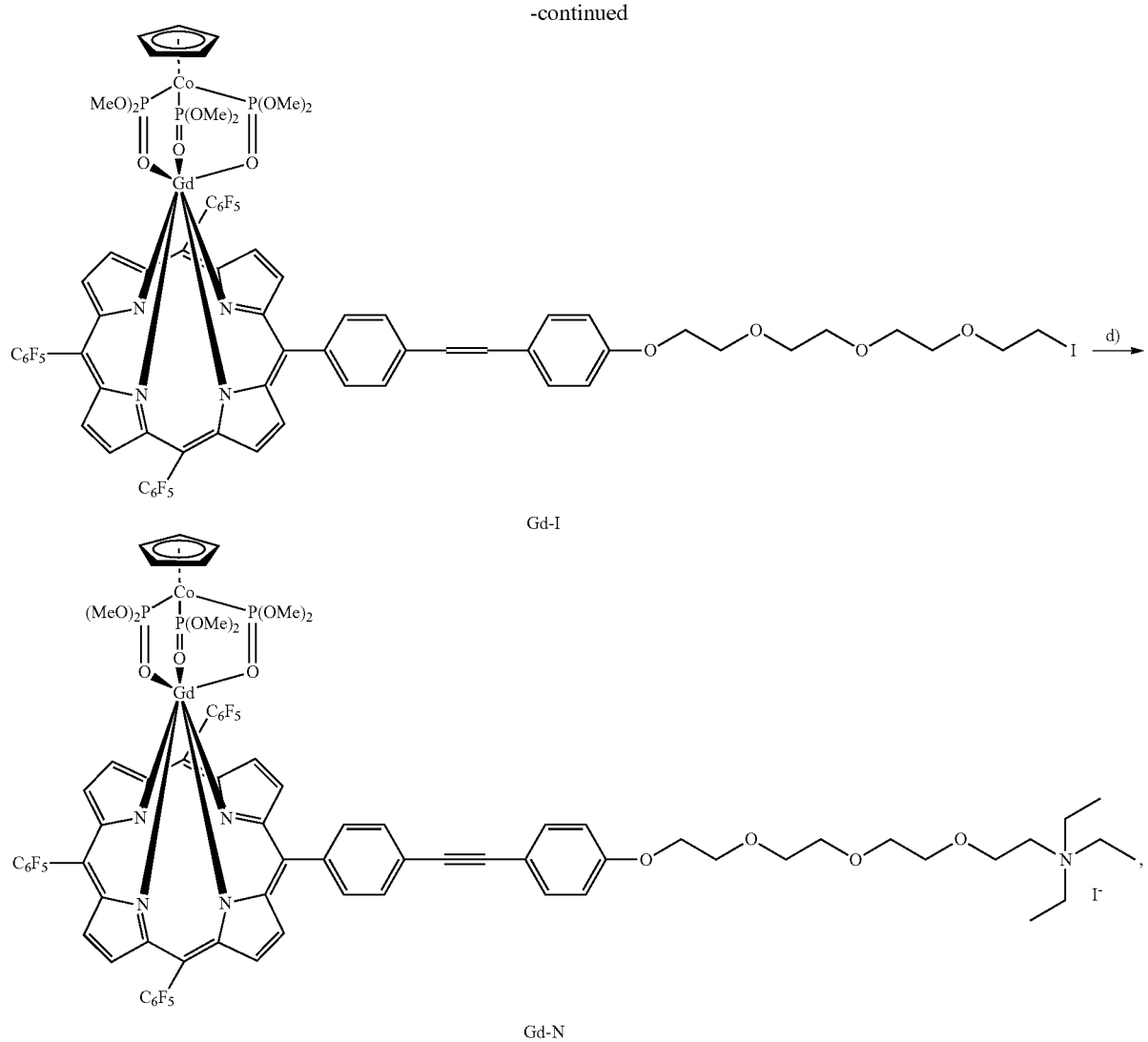

Gd-I

Gd-N wherein
said step (a) comprises:
removing the solvent from a solution of Gd[N(Si Me$_3$)$_2$]$_3$·[Li(THF)$_3$Cl]$_x$ to form a precipitation of LiCl;
adding dichloromethane (CH$_2$Cl$_2$) to the precipitation of LiCl to form a first mixture, wherein the first mixture is centrifuged to separate a clear layer from said first mixture;
transferring the clear layer to a porphyrin free base TFP-TMS dissolved in toluene solution to form a second mixture;
refluxing the second mixture until most of the free base is coordinated with the metal ion to form a refluxed second mixture;
cooling the refluxed second mixture to room temperature to form a cooled refluxed second mixture;
adding dry Na{(η$^5$-C$_5$H$_5$)Co[P(=O)(OMe)$_2$]$_3$} to the cooled refluxed second mixture to form a third mixture;
stirring the third mixture; removing the solvent from the third mixture to form a first residue;
dissolving the first residue in CH$_2$Cl$_2$ to form a fourth mixture;

filtering and column chromatographing the fourth mixture using CH$_2$Cl$_2$/Hexane as eluent to produce Gd-TMS; and
said step (b) comprises:
adding tetrabutylammonium fluoride to a solution of the Gd-TMS in CH$_2$Cl$_2$ and stirring the solution to create a chemical reaction;
after completion of the chemical reaction, the solution is passed through column chromatography to form a fifth mixture;
removing solvent from the fifth mixture to obtain an intermediate;
dissolving the intermediate and 4-iodophenol in dry tetrahydrofuran and triethylamine to form a sixth mixture
mixing the sixth mixture with nitrogen to form a nitrogenized sixth mixture;
adding Pd(PPh$_3$)$_4$ and CuI to said nitrogenized sixth mixture to form a seventh mixture;
stirring the seventh mixture at least 35° C. for at least 10 hours under a nitrogen atmosphere to produce a stirred seventh mixture;
removing the solvent from the stirred seventh mixture to produce a second residue;

purifying the second residue using column chromatography with $CH_2Cl_2$/Methanol as eluent to produce Gd—OH; and said step (c) comprises:

adding anhydrous $K_2CO_3$ to a solution of Gd—OH and tetraethyleneglycol diiodide in dry N,N-Dimethylmethanamide to form an eighth mixture;

heating said eighth mixture to at least 80° C. for at least 8 hours under a nitrogen atmosphere to form a heated eighth mixture;

removing the solvent from the heated eighth mixture to form a first crude product;

purifying the first crude product using column chromatography eluented by $CH_2Cl_2/CH_3OH$ to produce Gd—I, and said step (d) comprises:

adding anhydrous $NEt_3$ to a solution of Gd—I in dry DMF to form a ninth mixture;

heating the ninth mixture to at least 85° C. for at least 24 hours under nitrogen atmosphere to form a heated ninth mixture;

removing the solvent from the heated ninth mixture to obtain a second crude product;

purifying the second crude product using column chromatography with $CH_2Cl_2/CH_3OH$ as the eluent to remove unreacted Gd—I and other impurities, then further purifying with $CH_2Cl_2/CH_3OH$ as the eluent to obtain Gd—N.

7. The method according to claim 6 wherein the steps of removing the solvent from a given mixture or solution is done in a vacuum.

8. The method according to claim 6 wherein the process of mixing the sixth mixture with nitrogen to form a nitrogenized sixth mixture in step b) is by bubbling nitrogen gas in said sixth mixture for at least 30 minutes.

9. The method according to claim 6 wherein the process of using column chromatography in steps a) to d) are column chromatography on silica gel.

10. The method according to claim 6 wherein volume/volume of the column chromatography with $CH_2Cl_2/CH_3OH$ of step (d) is first 80:1 and followed by 10:1.

\* \* \* \* \*